(12) United States Patent
Adams et al.

(10) Patent No.: US 6,736,270 B2
(45) Date of Patent: May 18, 2004

(54) GLUED SCREENS FOR SHALE SHAKERS

(75) Inventors: Thomas C. Adams, Hockley, TX (US); Kerry Ward, Cypress, TX (US); Kenneth W. Seyffert, Houston, TX (US); David W. Largent, Cleveland, TX (US); David L. Schulte, Jr., Broussard, LA (US); Charles N. Grichar, Houston, TX (US); Vincent D. Leone, Houston, TX (US); Jefrey E. Walker, Lafayette, LA (US); Guy L. McClung, III, Spring, TX (US)

(73) Assignee: Varco I/P, Inc., Houston, TX (US)

( * ) Notice: Subject to any disclaimer, the term of this patent is extended or adjusted under 35 U.S.C. 154(b) by 313 days.

(21) Appl. No.: 10/087,025

(22) Filed: Oct. 19, 2001

(65) Prior Publication Data

US 2002/0130064 A1 Sep. 19, 2002

Related U.S. Application Data

(63) Continuation-in-part of application No. 09/603,531, filed on Jun. 27, 2000, now Pat. No. 6,450,345, which is a continuation-in-part of application No. 09/517,212, filed on Mar. 2, 2000, now Pat. No. 6,565,698, which is a continuation-in-part of application No. 09/454,722, filed on Dec. 4, 1999, now abandoned, which is a continuation-in-part of application No. 09/390,231, filed on Sep. 3, 1999, now Pat. No. 6,325,216, which is a continuation-in-part of application No. 09/707,277, filed on Nov. 6, 2000, which is a continuation-in-part of application No. 09/183,004, filed on Oct. 30, 1998, now Pat. No. 6,186,337.

(51) Int. Cl.[7] .............................................. B07B 1/49
(52) U.S. Cl. ................................... 209/399; 156/291
(58) Field of Search ............................... 209/399, 397, 209/401, 403; 156/290, 208, 210, 308.2, 308.4, 291

(56) References Cited

U.S. PATENT DOCUMENTS

| 40,242 A | 10/1863 | Capell |
| 236,416 A | 1/1881 | Bourne |
| 246,144 A | 8/1881 | Keeler |

(List continued on next page.)

FOREIGN PATENT DOCUMENTS

| EP | 0 169698 | 8/1993 | |
| GB | 269877 | 4/1928 | ................ 8794/27 |
| GB | 519680 | 4/1940 | |
| GB | 823648 | 11/1959 | |

(List continued on next page.)

OTHER PUBLICATIONS

Mud Equipment Manual Handbook 3: Shale Shakers, Brandt & Love, Gulf Pub. Co., 1982.

(List continued on next page.)

*Primary Examiner*—Kenneth W. Noland
(74) *Attorney, Agent, or Firm*—Guy McClung

(57) ABSTRACT

Screens and screen assemblies for a vibratory separator or shale shaker, such screens and screen assemblies made by a method including applying glue in a glue pattern to at least one layer of screening material, said applying done by powered moving mechanical glue application apparatus; in one aspect moving with powered mechanical screen movement apparatus the at least one layer of screening material beneath the powered moving mechanical glue application apparatus; in one aspect, using hot melt moisture-curing glue, and in one aspect facilitating the cure of moisture-curing glue by applying moisture to it.

30 Claims, 24 Drawing Sheets

U.S. PATENT DOCUMENTS

| | | | |
|---|---|---|---|
| 268,491 A | 12/1882 | Hubbell | |
| 275,190 A | 4/1883 | Gilbert | |
| 275,340 A | 4/1883 | Kimball | |
| 500,302 A | 6/1893 | Stoecket et al. | |
| 516,673 A | 3/1894 | Wilson | |
| 526,562 A | 9/1894 | Cross | |
| 560,858 A | 5/1896 | Missroon | |
| 583,981 A | 6/1897 | Plaisted | |
| 607,598 A | 7/1898 | Closz | |
| 777,317 A | 12/1904 | Traylor | |
| 865,185 A | 9/1907 | Kerrigan | |
| 948,222 A | 2/1910 | Honabach | |
| 964,897 A | 7/1910 | Bryant | |
| 966,578 A | 8/1910 | Murphy et al. | 209/401 X |
| 984,866 A | 2/1911 | Tate | |
| 1,098,979 A | 6/1914 | Schuchard | |
| 1,132,667 A | 3/1915 | Milliot | |
| 1,139,041 A | 5/1915 | Larson | |
| 1,242,982 A | 10/1917 | Reynolds | |
| 1,248,081 A | 11/1917 | Couch | |
| 1,250,768 A | 12/1917 | Baumgartner | 209/392 |
| 1,344,747 A | 6/1920 | Wright | |
| 1,397,339 A | 11/1921 | Sturtevant | |
| 1,423,021 A | 7/1922 | Reynolds | |
| 1,462,804 A | 7/1923 | Evans | |
| 1,505,735 A | 8/1924 | Stebbins | |
| 1,561,632 A | 11/1925 | Woodward | |
| 1,626,774 A | 5/1927 | Allan | |
| 1,614,586 A | 10/1927 | Anderson et al. | |
| 1,678,941 A | 7/1928 | Helman | |
| 1,713,143 A | 5/1929 | Overstrom | |
| 1,716,758 A | 6/1929 | Bland | |
| 1,785,195 A | 12/1930 | Hoes et al. | |
| 1,879,377 A | 9/1932 | McNeely | |
| 1,947,307 A | 2/1934 | Rafton | |
| 1,950,861 A | 3/1934 | O'Toole, Sr. | |
| 1,997,713 A | 4/1935 | Boehm | |
| 1,997,740 A | 4/1935 | Nickerson | |
| 2,052,467 A | 8/1936 | Hermann | 209/401 |
| 2,061,850 A | 11/1936 | Roberts | |
| 2,082,513 A | 6/1937 | Roberts | |
| 2,089,548 A | 8/1937 | Frantz et al. | |
| 2,104,785 A | 1/1938 | Akeyson | 210/384 |
| 2,190,262 A | 2/1940 | Geist | |
| 2,251,909 A | 8/1941 | Lindsay | 210/149 |
| 2,274,700 A | 3/1942 | Jenks | |
| 2,335,084 A | 11/1943 | Rice | 209/408 |
| 2,406,051 A | 8/1946 | Weiss | |
| 2,462,878 A | 3/1949 | Logue | |
| 2,480,320 A | 8/1949 | Carrier | 210/388 |
| 2,511,239 A | 6/1950 | Behnke et al. | 209/403 |
| 2,648,441 A | 8/1953 | Soldan | |
| 2,667,975 A | 2/1954 | Seaholm | 210/152 |
| 2,670,079 A | 2/1954 | Betts | 209/405 |
| 2,677,462 A | 5/1954 | Conkling | 209/403 |
| 2,723,032 A | 11/1955 | Gisler et al. | |
| 2,726,184 A | 12/1955 | Cox et al. | |
| 2,774,477 A | 12/1956 | Pollitz | 209/403 |
| 2,800,227 A | 7/1957 | Kiger | 209/412 X |
| 2,813,629 A | 11/1957 | Brugmann | 209/403 |
| 2,827,169 A | 3/1958 | Cusi | |
| 2,902,165 A | 9/1959 | Imershein | |
| 2,929,464 A | 3/1960 | Sprouse | |
| 2,973,865 A | 3/1961 | Cibula | 209/392 X |
| 2,980,208 A | 4/1961 | Neumann | |
| 2,985,303 A | 5/1961 | Wright | |
| 3,057,481 A | 10/1962 | Pale | 210/493 |
| 3,070,231 A | 12/1962 | McCorkel et al. | 209/319 |
| 3,092,573 A | 6/1963 | Lambert et al. | 209/403 |
| 3,165,473 A | 1/1965 | Pall et al. | 210/510 |
| 3,176,843 A | 4/1965 | Hoskins et al. | 209/403 |
| 3,243,943 A | 4/1966 | Getzin | 55/499 |
| 3,255,885 A | 6/1966 | Burls | 209/314 |
| 3,285,413 A | 11/1966 | Taylor-Smith | |
| 3,306,794 A | 2/1967 | Humbert, Jr. | |
| 3,458,978 A | 8/1969 | Davis | 55/499 |
| 3,465,413 A | 9/1969 | Rosaen et al. | 29/428 |
| 3,542,636 A | 11/1970 | Wandel | |
| 3,574,103 A | 4/1971 | Latkin | 428/72 |
| 3,655,060 A | 4/1972 | Hagdahl | 210/493 |
| 3,679,057 A | 7/1972 | Perez | 210/223 |
| 3,716,138 A | 2/1973 | Lumsden | 209/401 |
| 3,747,770 A | 7/1973 | Zentis | 210/402 |
| 3,747,772 A | 7/1973 | Brown | 210/493 |
| 3,789,498 A | 2/1974 | Cole | 29/470.9 |
| 3,793,692 A | 2/1974 | Tate et al. | 29/163.5 |
| 3,853,529 A | 12/1974 | Boothe et al. | 55/499 |
| 3,900,628 A | 8/1975 | Stewart | |
| 3,929,642 A | 12/1975 | Ennis et al. | 210/113 |
| 3,970,549 A | 7/1976 | Ennis et al. | 209/341 |
| 4,019,987 A | 4/1977 | Krashow | 210/232 |
| 4,022,596 A | 5/1977 | Pedersen | 55/528 |
| 4,033,865 A | 7/1977 | Derrick, Jr. | 209/275 |
| 4,062,769 A | 12/1977 | Simonson | 209/399 |
| 4,065,382 A | 12/1977 | Derrick, Jr. | 209/313 |
| 4,075,106 A | 2/1978 | Yamazaki | 210/487 |
| 4,138,303 A | 2/1979 | Taylor, Sr. | 156/264 |
| 4,224,146 A | 9/1980 | Kent et al. | 209/243 |
| 4,306,974 A | 12/1981 | Harry | 210/388 |
| 4,375,199 A | 3/1983 | Graeme-Barber et al. | 144/222 |
| 4,380,494 A | 4/1983 | Wilson | 209/319 |
| 4,410,427 A | 10/1983 | Wydeven | 210/317 |
| 4,446,022 A | 5/1984 | Harry | 210/388 |
| 4,457,839 A | 7/1984 | Bailey | 209/234 |
| 4,464,242 A | 8/1984 | Boulton | 204/253 |
| 4,472,473 A | 9/1984 | Davis et al. | 428/184 |
| 4,546,783 A | 10/1985 | Lott | 134/109 |
| 4,575,421 A | 3/1986 | Derrick et al. | 209/397 |
| 4,582,597 A | 4/1986 | Huber | 204/313 |
| 4,589,983 A | 5/1986 | Wydevan | 210/317 |
| 4,603,653 A | 8/1986 | Bews | 116/209 |
| 4,617,122 A | 10/1986 | Kruse et al. | 210/493.3 |
| 4,634,535 A | 1/1987 | Lott | 210/780 |
| 4,678,578 A | 7/1987 | Nodes et al. | 210/445 |
| 4,696,751 A | 9/1987 | Eifling | 210/780 |
| 4,728,422 A | 3/1988 | Bailey | 210/314 |
| 4,744,898 A | 5/1988 | Bailey | 210/236 |
| 4,769,968 A | 9/1988 | Davis et al. | 52/814 |
| 4,819,809 A | 4/1989 | Derrick | 209/275 |
| 4,820,407 A | 4/1989 | Lilie | 209/397 |
| 4,832,834 A | 5/1989 | Baird, Jr. | 209/397 |
| 4,846,352 A | 7/1989 | Bailey | 209/399 |
| 4,857,176 A | 8/1989 | Derrick et al. | 209/392 |
| 4,882,054 A | 11/1989 | Derrick et al. | 210/389 |
| 4,940,500 A | 7/1990 | Tadokoro et al. | 156/204 |
| 4,954,249 A | 9/1990 | Gero et al. | 209/273 |
| 5,028,474 A | 7/1991 | Czaplicki | 428/178 |
| 5,084,178 A | 1/1992 | Miller et al. | 210/493.5 |
| 5,116,553 A | 5/1992 | Harvey | 264/39 |
| 5,137,622 A | 8/1992 | Souter | 209/403 |
| 5,139,154 A | 8/1992 | Gero et al. | 209/273 |
| 5,162,143 A | 11/1992 | Porter et al. | 428/179 |
| 5,167,740 A | 12/1992 | Michaelis et al. | 156/73.1 |
| 5,211,291 A | 5/1993 | Kelley et al. | 209/680 |
| 5,221,008 A | 6/1993 | Derrick, Jr. et al. | 209/269 |
| 5,240,479 A | 8/1993 | Bachinski | 55/103 |
| 5,256,292 A | 10/1993 | Cagle | 210/499 |
| 5,312,508 A | 5/1994 | Chisholm | 156/292 |
| 5,316,676 A | 5/1994 | Drori | 210/411 |
| 5,330,057 A | 7/1994 | Schiller et al. | 209/392 |
| 5,385,669 A | 1/1995 | Leone, Sr. | 210/488 |

| | | | |
|---|---|---|---|
| 5,392,925 A | 2/1995 | Seyffert | 209/405 |
| 5,417,793 A * | 5/1995 | Bakula | 156/308.2 |
| 5,417,858 A | 5/1995 | Derrick et al. | 210/388 |
| 5,417,859 A | 5/1995 | Bakula | 210/388 |
| H1481 H | 9/1995 | Ray | 428/98 |
| 5,490,598 A | 2/1996 | Adams | 209/403 X |
| 5,614,094 A | 3/1997 | Deister et al. | 210/388 |
| 5,626,234 A | 5/1997 | Cook et al. | 209/315 |
| 5,636,749 A | 6/1997 | Wojciechowski | 209/403 |
| 5,667,661 A | 9/1997 | Hughes | 205/138 |
| 5,690,826 A | 11/1997 | Cravello | 210/384 |
| 5,720,881 A | 2/1998 | Derrick et al. | 210/308 |
| 5,783,077 A | 7/1998 | Bakula | 210/388 |
| 5,814,218 A | 9/1998 | Cagle | 210/388 |
| 5,819,952 A | 10/1998 | Cook et al. | 209/400 |
| 5,851,393 A | 12/1998 | Carr et al. | 204/489 |
| 5,868,929 A | 2/1999 | Derrick et al. | 210/388 |
| 5,876,552 A | 3/1999 | Bakula | 156/308.2 |
| 5,921,399 A | 7/1999 | Bakula et al. | 209/272 |
| 5,927,511 A | 7/1999 | Riddle et al. | 209/405 |
| 5,944,197 A | 8/1999 | Baltzer et al. | 209/400 |
| 5,944,993 A | 8/1999 | Derrick et al. | 210/388 |
| 5,950,841 A | 9/1999 | Knox et al. | 209/315 |
| 5,958,236 A | 9/1999 | Bakula | 210/388 |
| 5,967,336 A | 10/1999 | Baltzer et al. | 209/403 |
| 5,984,107 A | 11/1999 | Bleh | 209/320 |
| 5,992,641 A | 11/1999 | Caldwell, Jr. | 209/273 |
| 6,000,556 A | 12/1999 | Bakula | 210/388 |
| 6,000,558 A | 12/1999 | Proulx et al. | 210/486 |
| 6,006,923 A | 12/1999 | Helmy et al. | 209/397 |
| 6,018,383 A | 1/2000 | Dunn et al. | 355/49 |
| 6,019,152 A | 2/2000 | Haynes et al. | 156/433 |
| 6,019,228 A | 2/2000 | Duggan | 209/408 |
| 6,053,331 A | 4/2000 | Cravello | 210/388 |
| 6,053,332 A | 4/2000 | Bakula | 210/388 |
| 6,186,337 B1 | 2/2001 | Adams et al. | 209/401 |
| 6,269,954 B1 | 8/2001 | Baltzer | 209/405 |
| 6,279,644 B1 | 8/2001 | Wylie | 160/371 |

FOREIGN PATENT DOCUMENTS

| | | | |
|---|---|---|---|
| GB | 1412975 | | 11/1975 |
| GB | 1575312 | | 9/1980 |
| GB | 1578948 | | 11/1980 |
| GB | 2124099 | A | 2/1984 |
| GB | 2085744 | | 6/1984 |
| GB | 2161715 | A | 1/1986 |
| GB | 2162091 | | 1/1988 |
| GB | 21617158 | | 6/1988 |
| GB | 2161715 | | 6/1988 |
| GB | 2175222 | | 4/1989 |
| GB | 2206501 | | 11/1990 |
| GB | 2312858 | | 3/2000 |
| JP | 59-142818 | | 8/1984 |
| WO | PCT/GB91/00957 | | 1/1991 |
| WO | PCT/US94/00243 | | 1/1994 | |
| WO | WO 95/23655 | | 3/1994 | B07B/1/46 |
| WO | PCT/EP96/03103 | | 2/1996 | |

OTHER PUBLICATIONS

An Innovative Method of ranking Shale Shaker Screens, STC05, Shale Shaker Technology Conference, Feb. 1991.
U.S. application Ser. No. 08/282,983; filed Jul. 29, 1994 entitled "Shale Shaker Screens," co–owned with present invention/application.
"Derrick Sandwich Shaker," Derrick Equipment Co. (Prior to 1992).
"The Future of Fine Screening," Derrick Equipment Co. 1993.
"Derrick Pyramid Screens," Derrick Corp.
"Advanced Wirecloth, Inc.," Advanced Wirecloth, Inc., 1993.
"CPI Group, Inc.," CPI Group, Inc., 1990.
"LM3 Full–Flo Shale Shaker," Sweco Oilfield Services, 1991.
Pending U.S. Application 08/220,101 filed Mar. 30, 1994 entitled "Screen For Vibrating Separator."
Amendment Under 37 CFR 1.115 in pending U.S. S.N. 08/220,101.
Mcnally Coal Preparation Manual M 576, pp. 111,73–96, 216 (1978).
Layered Shale Shaker Screens Improve Mud Solids Control, World Oil, 1978.
Int'l Search Report, PCT/GB97/00385 co–owned with present application.
Official Gazette Entry for U.S. Pat. No. 5,626,234, May 6, 1997.
The Brandt Company General Catalog 1982–1983, 4 pages, 1982.
Take the Drilled Solids Out, The Brandt Company, Sep. 1980.
Sweco Full–Flow, Sweco, Inc. 1992.
Catalog 105 H&K Perforated Materials, Harrington & King-Perforating Co., 1988.
Sweco Oilfield Services, Composite Catalog, 1992.
Screening Equipment Handbook, Pankratz, 1988.
Supertaut Mud Cleaner Screens, Sweco Oilfield Services, 1992.
Filtration & Separation, Flo Trend Systems, Inc. 1989.
Clean Liquids/Dry Solids, Flo Trend Systems, Inc. 1989.
H & K Perforated Materials, Harrington and King, Catalog 105, 1988.

* cited by examiner

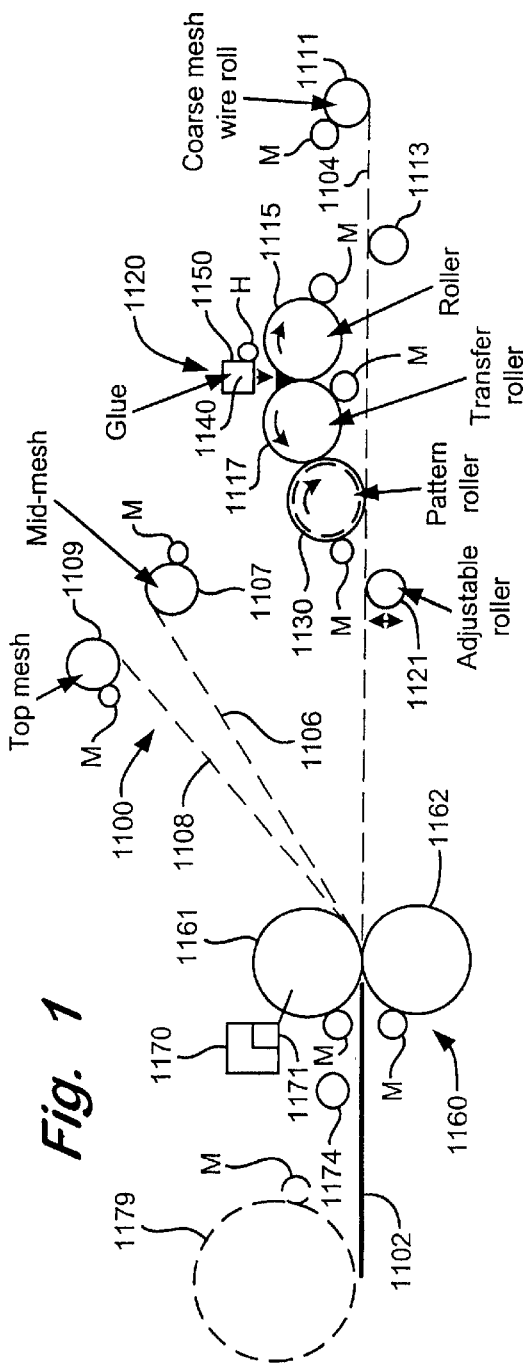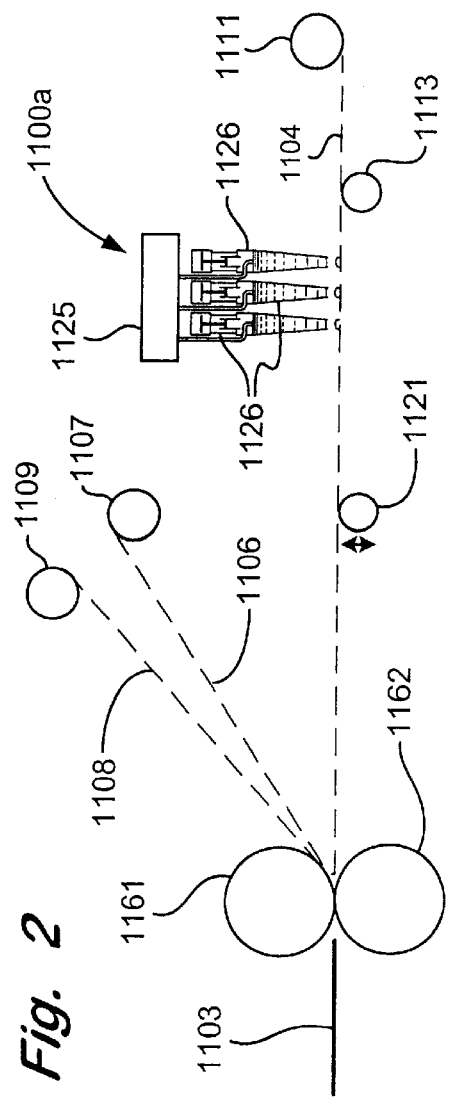

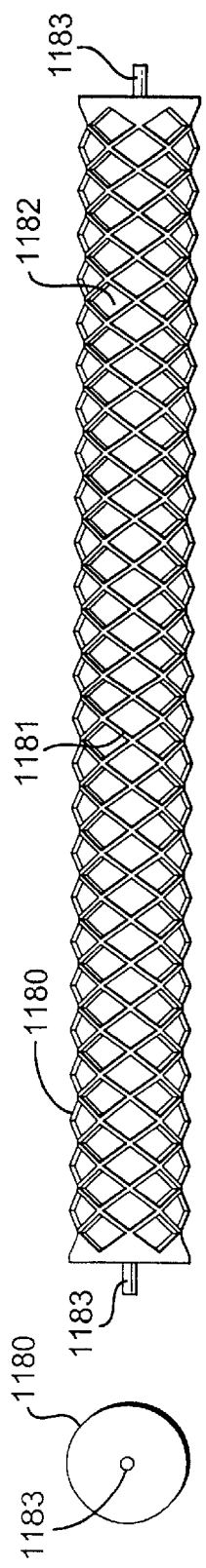
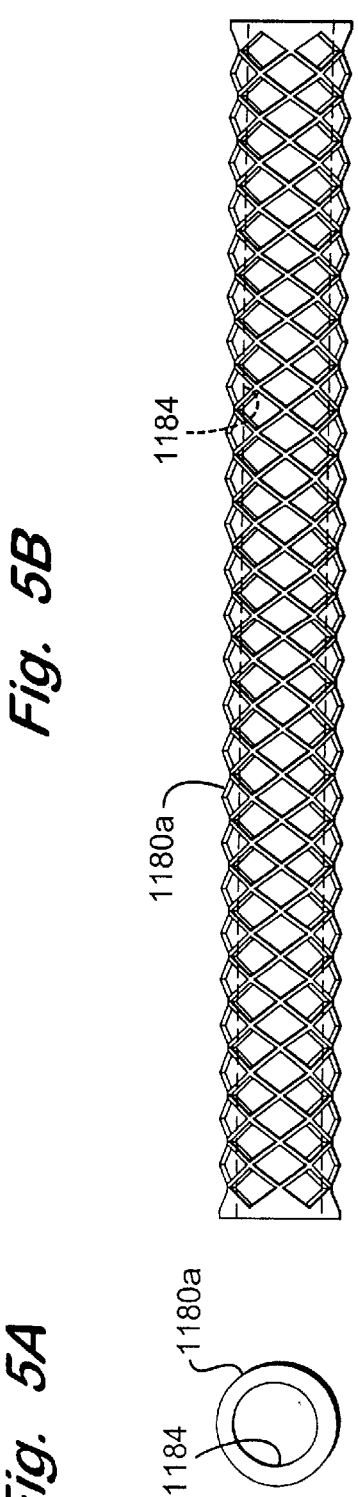
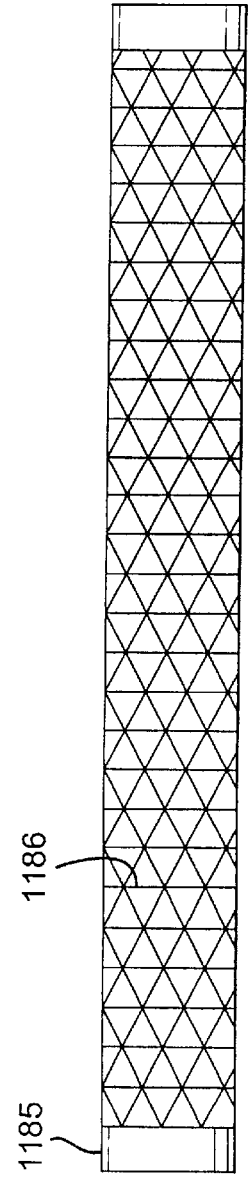
Fig. 5A  Fig. 5B  Fig. 6A  Fig. 6B  Fig. 7

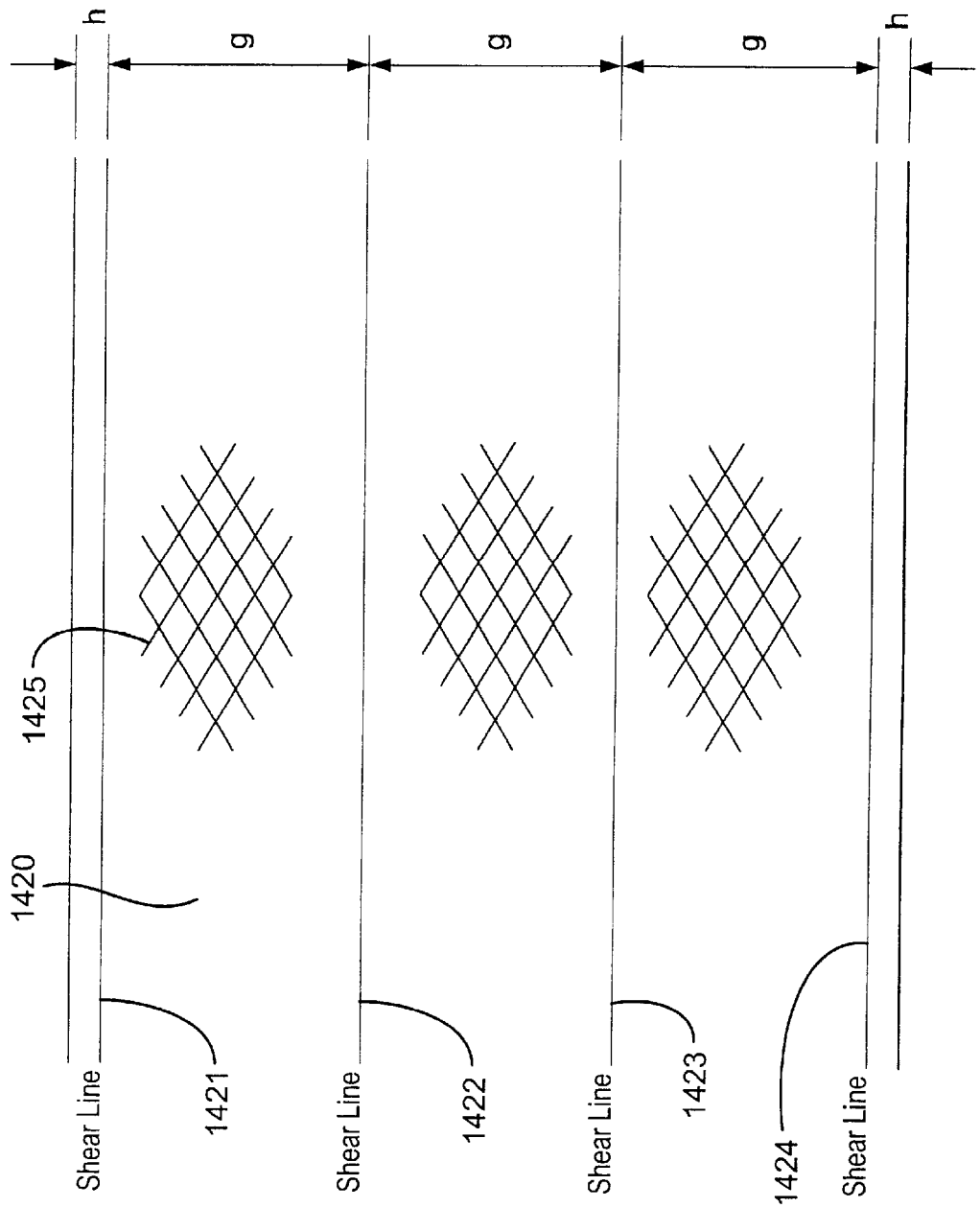

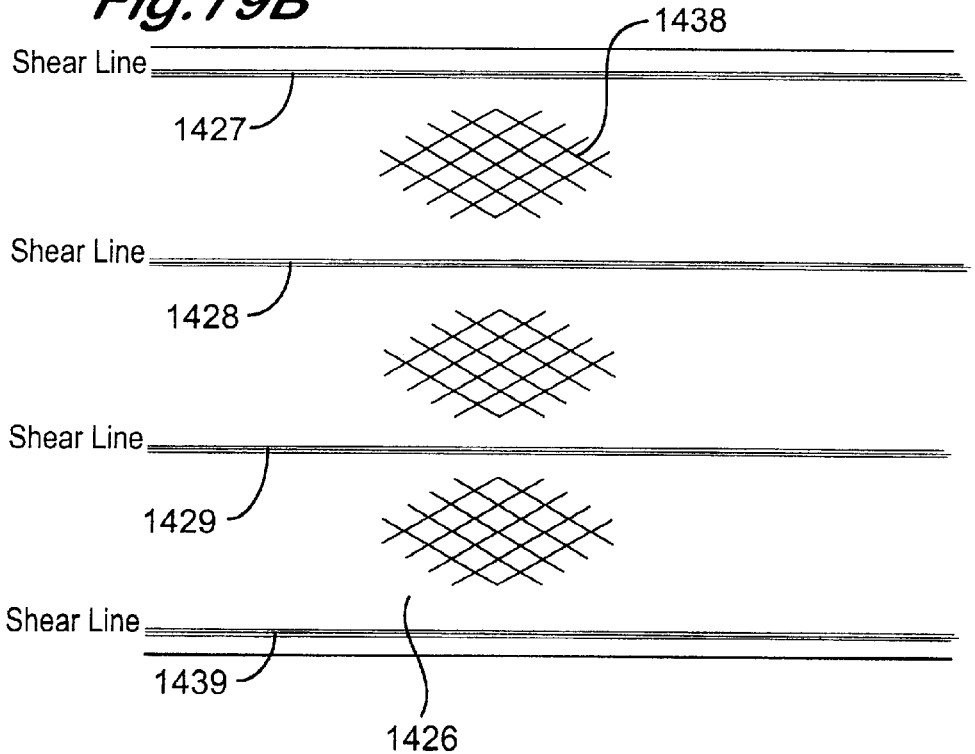
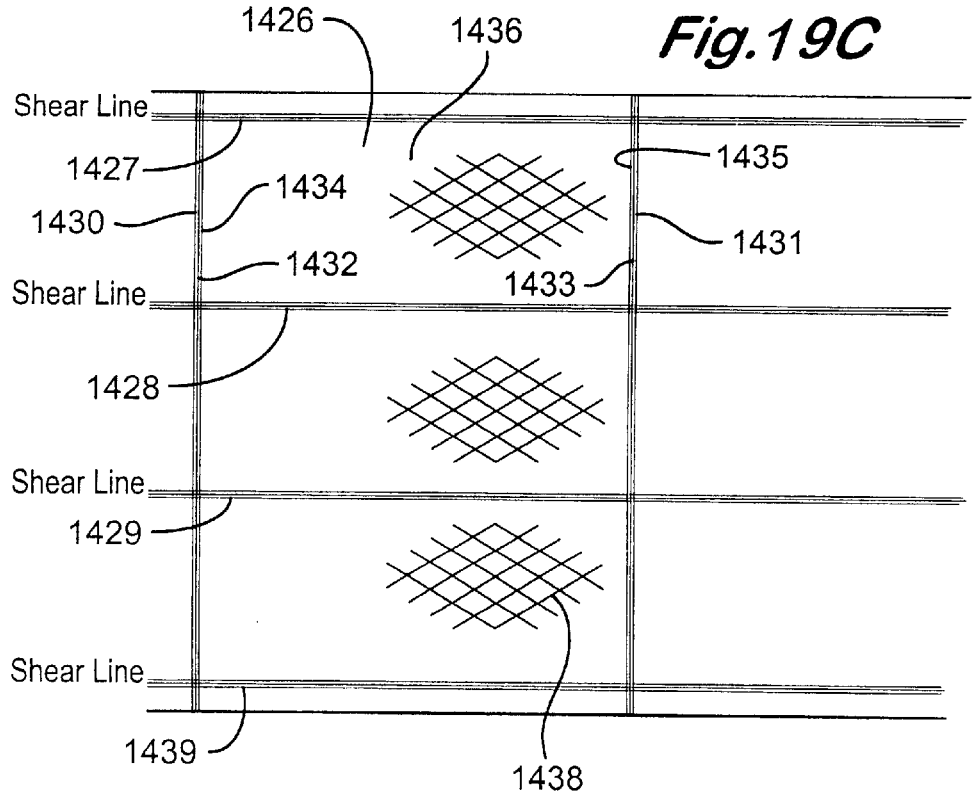

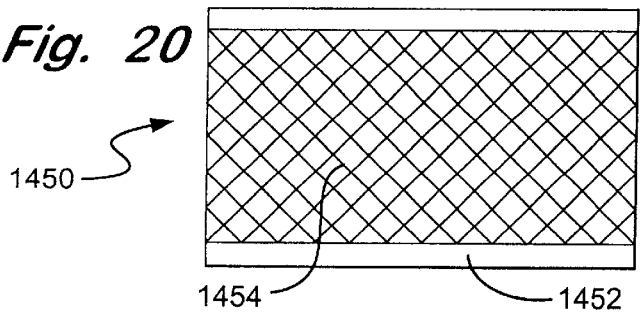
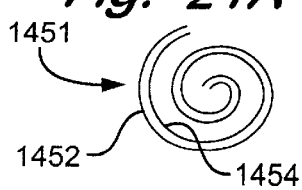
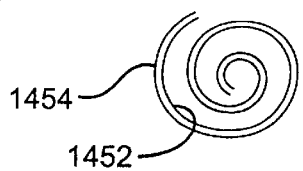
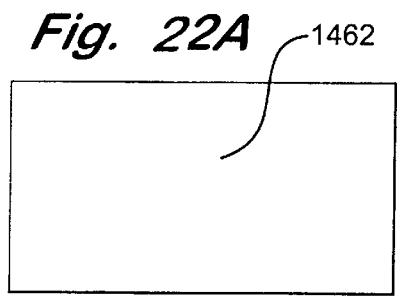
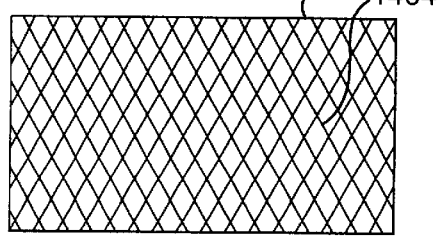
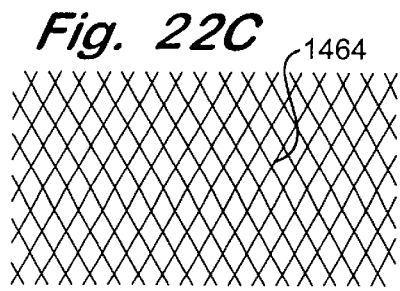
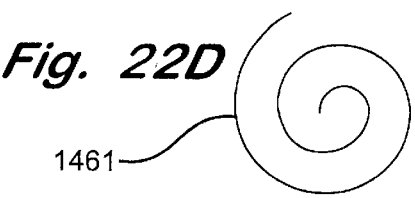
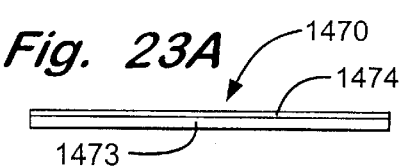
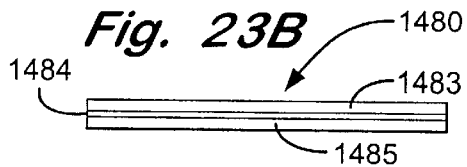
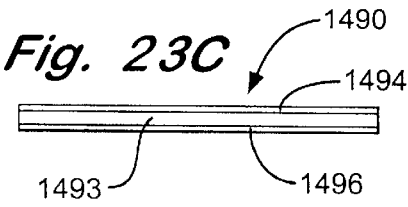
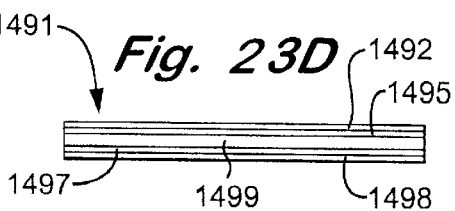

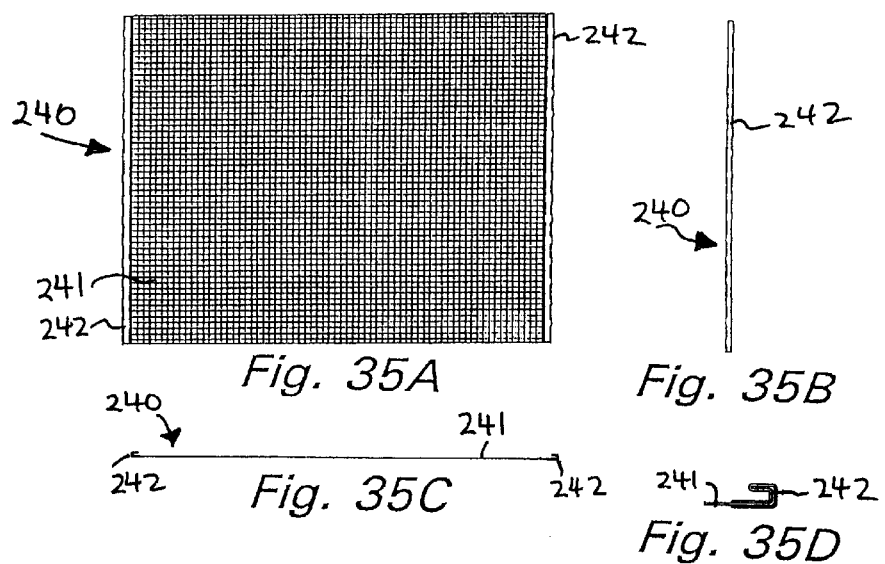
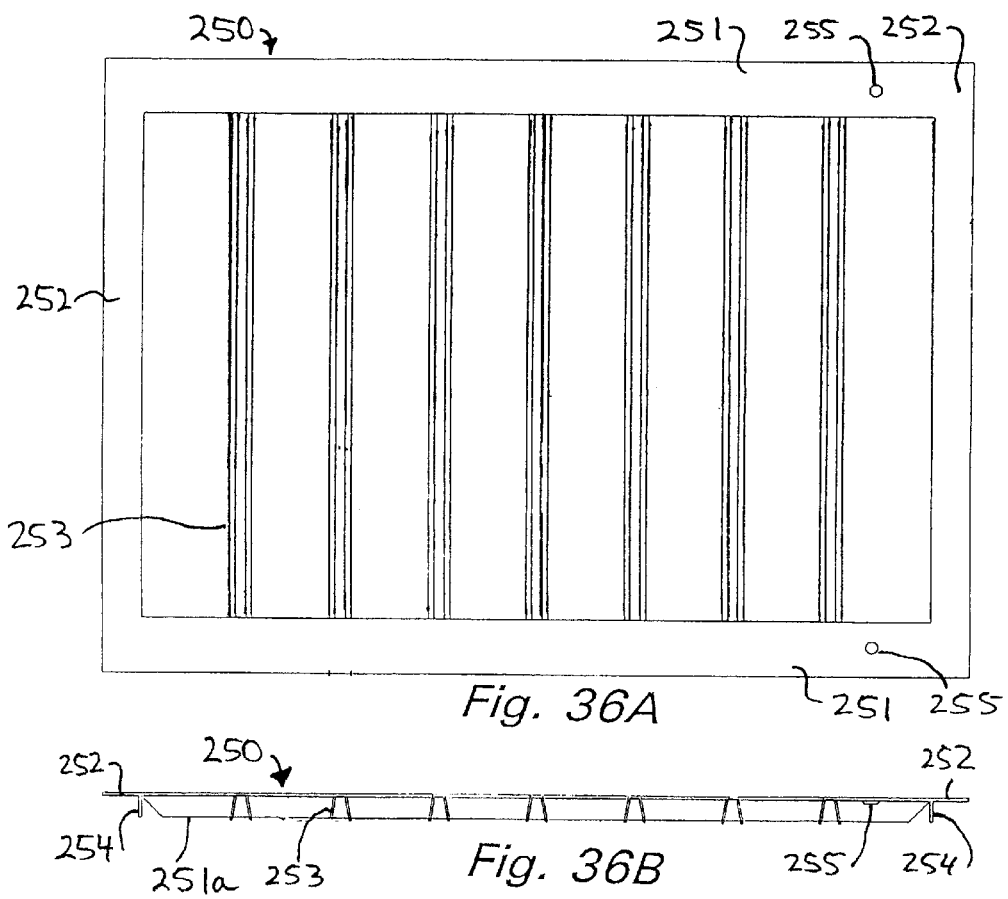

GLUED SCREENS FOR SHALE SHAKERS

RELATED APPLICATIONS

This application is a continuation-in-part of U.S. application. Ser. No. 09/603,531 filed Jun. 27, 2000 now U.S. Pat. No. 6,450,345 which is a continuation-in-part of U.S. application Ser. No. 09/517,212 filed Mar. 2, 2000 now U.S. Pat. No. 6,565,698 which is a continuation-in-part of U.S. application Ser. No. 09/454,722 filed on Dec. 4, 1999 now abandoned which is a continuation-in-part of U.S. application Ser. No. 09/390,231 filed Sep. 3, 1999 U.S. Pat. No. 6,325,216; and this application is a continuation-in-part of U.S. application Ser. No. 09/707,277 filed Nov. 6, 2000 which is a continuation-in-part of U.S. application Ser. No. 09/183,004 filed Oct. 30, 1998 issued as U.S. Pat. No. 6,186,337 on Feb. 13, 2001—all of which applications and patents are incorporated herein in their entirety for all purposes and with respect to all of which the present invention claims priority under the Patent Laws.

BACKGROUND OF THE INVENTION

1. Field of the Invention

The present invention is directed to glued screens for vibratory separator apparatuses and shale shakers; to methods for making such screens; to automated methods for making such screens; to screens made by such methods; to machines for making such screens, and to vibratory separator apparatuses and shale shakers with such screens.

2. Description of Related Art

The need for solids control in drilling mud used in hydrocarbon well drilling is well known in the prior art. Drilling mud, typically a mixture of clay and water and various additives, is pumped down through a hollow drill string (pipe, drill collar, bit, etc.) into a well being drilled and exits through holes in a drillbit. The mud picks up cuttings (rock) and other solids from the well and carries them upwardly away from the bit and out of the well in a space between the well walls and the drill string. At the top of the well, the solids-laden mud is discharged over a shale shaker, a device which typically has a series of screens arranged in tiered or flat disposition with respect to each other. The prior art discloses a wide variety of vibrating screens, devices which use them, shale shakers, and screens for shale shakers. The screens catch and remove solids from the mud as the mud passes through them. If drilled solids are not removed from the mud used during the drilling operation, recirculation of the drilled solids can create weight, viscosity, and gel problems in the mud, as well as increasing wear on mud pumps and other mechanical equipment used for drilling.

SUMMARY OF THE PRESENT INVENTION

The present invention, in certain aspects discloses a screen assembly with layers glued together by, e.g., heated (then cured) moisture-curing hot melt glue, and methods for producing such glued screen assemblies.

The present invention, in certain aspects, provides a screen assembly made by an automated method according to the present invention. In certain embodiments of such methods moving mechanical apparatus powered e.g. by electricity or by fluid driven power apparatus (e.g. but not limited to, apparatus powered by fluid under pressure, e.g., but not limited to, hydraulic fluid under pressure powering hydraulic pumps and/or motors) applies glue in a desired pattern to one, two, three or more layers of screening material. Upon curing, the glue holds together screen assemblies according to the present invention which have one, two or more layers of screening material, bonded together or not, connected together or not, with or without a lower support structure, and with or without side hookstrip mounting apparatus. Any suitable screening material disclosed herein or disclosed in any patent or application referred to herein may be used. In one aspect screening material is used suitable for a screen assembly for screening drilling fluid introduced to a shale shaker that has one or more such screen assemblies. In certain aspects the glue used for applying a glue pattern is such that it rests on top of the screening material even in an uncured or un-set state and does not full through or out from the screening material and rests on it for further steps in the method, or is such that if it does tend to move downwardly through layer(s) of screening material its rate of movement is such that (and it is sufficiently viscous and/or it is sufficiently cured) it does not fall out from the screening assembly.

In certain methods that are automated according to the present invention, powered mechanical movement apparatus moves the layer(s) of screening material with respect to glue application apparatus. In one aspect the powered moving mechanical apparatus uses a patterned roller to apply glue in a pattern to screening material. In another aspect, one, two or a larger plurality of glue nozzles are moved above the screening material (which itself may be stationary or may be moving beneath the glue nozzles) to apply the glue in a desired pattern. In one particular aspect a plurality of spaced-apart glue dispensers on a manifold are moved above the screening material. In certain aspects the manifold is oscillated with respect to the screening material and, in one aspect, there are two, three or more such manifolds. Any desired glue pattern may be applied. A screen or screen assembly thus made according to the present invention may, optionally, be mounted to lower support, such as a tubular frame, on a strip support, rod support, on a layer of coarse mesh or gridwork, or on a perforated plate or perforated piece of sheet metal. Such mounting may be any suitable known method disclosed in the art and any suitable known frame, strip support, rod support, coarse layer, or perforated plate may be used—including, but not limited to, those disclosed in any patent or application referred to herein. Alternatively, according to the present invention, hookstrips may be applied on spaced-apart sides of glued screening material(s).

In certain aspects of methods according to the present invention glue is applied with at least two nozzles so that lines of glue intersect and, at points of intersection, the glue pattern is stronger (due to the fact there is relatively more glue present at such points) than at points along either glue line where the lines do not intersect.

The present invention discloses, in at least certain aspects, a screen made by a method for making a screen for a vibratory separator, the method including placing a substrate or at least one layer of screening material below a glue application apparatus, the glue application apparatus including a main body and a plurality of movable glue nozzles movably connected to the body, and applying with the movable glue nozzles an amount of glue in a pattern to at least a portion of the substrate or to the at least one layer of screening material by moving the movable glue nozzles over the substrate or over the at least one layer of screening material. In one such method in which a glue pattern is applied to a substrate, the glue pattern while still manipulable is removed from the substrate and is then applied in pattern form to screening material.

The present invention discloses, in certain embodiments, a screen for vibrating screen apparatus. The screen has one or more upper layers of screen, screen cloth, and/or mesh. The layer or layers may be mounted on frame apparatus which may include a solid side support on each of two spaced apart sides of the layer(s), or a full four sided screen frame, with or without one or more interior crossmembers such as tubular rods or hollow tubular members extending between the sides. A strip support or strips of support material (e.g. flat steel) may be used beneath screen layer(s). In some aspects, hookstrips are used on opposed sides or ends of a screen made by a method according to the present invention so that it can be mounted in a shaker or other separator apparatus. Any known hookstrip configuration may be used according to the present invention.

The present invention, in one embodiment includes a shale shaker with a frame; a "basket" or screen mounting apparatus; one or more screens according to the present invention as described above and below; and basket vibrating apparatus.

The present invention discloses, in certain aspects, a screen made by methods for making screens and screen assemblies as disclosed herein for a vibratory separator, the methods including placing at least two layers (in some cases two, three or four layers) of screening material adjacent one another one on top of the other, introducing an amount of glue to the at least two layers of screening material for adhering at least portions of them together, the amount of glue introduced to the at least two layers of screening material from one, two or more manifolds each with a plurality of glue dispensing nozzles or tubes above screen layer(s) moved beneath the manifolds.

It is, therefore, an object of at least certain preferred embodiments of the present invention to provide:

New, useful, unique, efficient, non-obvious screens made by methods for making screens and screen assemblies; screen assemblies with multiple layers of screening material; screen assemblies with one or more lower coarse screen members and one or more upper fine screen members; such screens with a lower support beneath the screen layers and, in one aspect, with one or more bottom strip members, support strips or rods; such screen assemblies with a lower support frame or a lower support perforated plate; such screen assemblies in which screening material of adjacent screen layers is glued together with glue, e.g. but not limited to, moisture-curing hot melt glue; and shale shakers or vibratory separators with any such screen assemblies;

Such screens made by an automated method with powered moving mechanical apparatus for applying heated glue in a pattern to one or more layers of screening material and, in one aspect, with powered mechanical apparatus for moving the screen layer(s) beneath the glue apparatus;

Such screens or screen assemblies made with a gluing system that has one, two or more manifolds each with a plurality of spaced-apart glue dispensers for applying a pattern of glue to screen layer(s) moving beneath the manifolds; and, in one aspect, with hot-melt glue sufficiently viscous to stay on a layer or layers of screening material to cure and glue the layers together;

A shale shaker or vibratory separator with one or more such screens or screen assemblies; and Methods of making such screens and machines for making them.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or equivalent embodiments.

FIGS. 1 and 2 are schematic views of apparatus according to the present invention for methods according to the present invention to make a screen according to the present invention.

FIG. 5A is an end view of a pattern roller according to the present invention. FIG. 5B is a side view of the roller of FIG. 5A.

FIG. 6A is an end view of a pattern roller according to the present invention. FIG. 6B is a side view of the roller of FIG. 6A.

FIGS. 7 and 8 are side views of pattern rollers according to the present invention.

FIGS. 19A–19D are top views of glue patterns according to the present invention.

FIG. 20 is a top view of a screen assembly component according to the present invention.

FIG. 21A is an end view of a rolled up screen component e.g. like the screen component of FIG. 20. FIG. 21B is an end view of a rolled up screen component e.g. like the screen component of FIG. 20.

FIG. 22A is a top view of a substrate for glue for a screen assembly according to the present invention. FIG. 222B is a top view that shows the substrate of FIG. 22A with a glue pattern according to the present invention deposited thereon. FIG. 22C shows the glue pattern of FIG. 22B removed from the substrate of FIG. 22A. FIG. 22D is an end view that shows the glue pattern of FIG. 22C in a roll.

FIG. 23A is a side view of a screen assembly according to the present invention. FIG. 23B is a side view of a screen assembly according to the present invention. FIG. 23C is a side view of a screen assembly according to the present invention. FIG. 23D is a side view of a screen assembly according to the present invention.

FIG. 35A is a top schematic view of a screen assembly according to the present invention. FIG. 35B is a side view and FIG. 35C is an end view of the screen assembly of FIG. 35A. FIG. 35D is an enlargement of a hookstrip side of the screen assembly as shown in FIG. 35C.

FIG. 36A is a top view of a screen support according to the present invention. FIG. 36B is a cross-section view along the length of the screen assembly of FIG. 36A.

DESCRIPTION OF EMBODIMENTS PREFERRED AT THE TIME OF FILING FOR THIS PATENT

Figure 3:
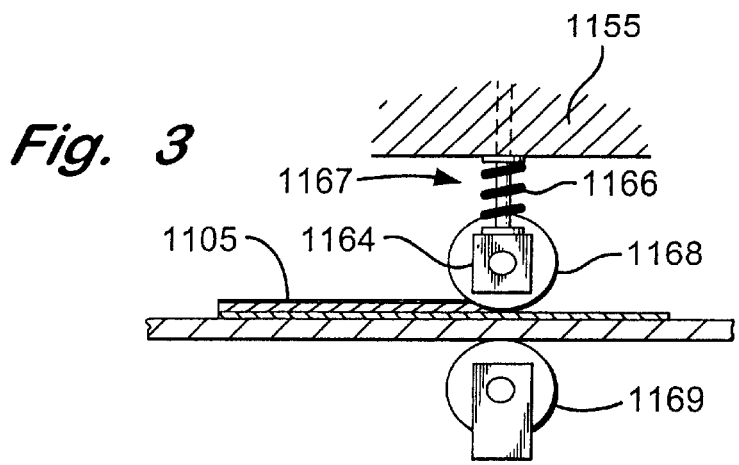
FIG. 3 is a side view of a roller apparatus for apparatus as in FIG. 1 or 2.

FIG. 1 shows a system 1100 according to the present invention for making a screen 1102 according to the present invention by a method according to the present invention. As shown the system 1100 produces a screen 1102 which includes a lower coarse mesh or screen 1004, an intermediate mesh or screen 1106, and a top mesh or screen 1108. Any one of these meshes (or screens) 1104, 1106, 1108 may be deleted. Alternatively one or more additional mesh layers may be added.

The coarse mesh 1104 is initially wound on a roller 1111 from which it is unwound and passes over a rotating roller 1113. From the roller 1113 the coarse mesh moves to a position beneath a gluing station 1120 where heated glue in a pattern is applied on the coarse mesh 1104. In one aspect the coarse mesh is 19 mesh made of wire with a diameter of about 0.126 inches. Of course any suitable mesh may be used. Sufficiently viscous hot melt glue is used which does not pass through and away from the mesh to which it is applied.

A pattern roller 1130 applies a layer of glue in a desired pattern onto the coarse mesh 1104. Glue 1140 from a reservoir/manifold 1150 flows to a space forming a "pond" of glue between a first roller 1115 and a transfer roller 1117. Either or both of these rollers may be a heated roller as is well known in the art. Alternatively, or in addition to heat from a heated roller or rollers, hot air from an optional heater H may be blown at the roller(s) and/or at the "pond", and/or it may heat the glue in the reservoir/manifold 1150. The transfer roller 1117 rotates counter-clockwise as viewed in FIG. 1 and the first roller 1115 rotates clockwise; thus a film of glue is deposited on the outer surface of the transfer roller 1117 which film, in turn, contacts parts of a pattern in or on an outer surface of the pattern roller 1130 which rotates clockwise as viewed in FIG. 1. The film on the pattern parts of the pattern roller 1130 is applied in the pattern onto the coarse mesh 1104 moving beneath the pattern roller 1130. In another aspect, glue is applied on top of a combination of two, three, or more meshes prior to entering between the rollers 1161 (rather than on top of the coarse mesh when it comes off the roll 1111). In another aspect, the glue is applied only to the mesh from either the roll 1109 or the roll 1107.

An adjustable roller 1121, whose tension against the mesh is adjustable by moving the roller up/down, supports the coarse mesh 1004 with glue thereon. The coarse mesh 1104 with glue thereon in a desired pattern determined by the pattern on the pattern roller 1130 advances to a pressing station 1160. The intermediate mesh 1106 is fed between rollers 1161 and 1162 of the pressing station 1160 from a roll 1107 as is the top mesh 1108 from a roll 1109.

Between the rollers 1161, 1162, the three meshes are pressed together and the glue is pressed between all three meshes to bond them together. Optionally, coolant fluid from a coolant reservoir 1170 is pumped with a pump 1171 through one or both of the rollers 1611, 1162 to cool the mesh combination passing between the rollers 1161, 1162. The finished screen 1102 (including all three meshes and glue) exit from between the rollers 1161, 1162. Optionally, a fan or fans and/or air movers or other cooling device(s) 1174 may be used to cool the screen 1102. In one aspect moisture-curing hot melt glue is used (e.g. but not limited commercially available Henkel R183B hot melt glue) and water is applied to the hot glue to facilitate the moisture-curing; e.g. water is poured, sprayed and/or misted onto the glue in combined and glued together layers of screening material.

The various meshes for the screen 1102 may be fed through the system 1100 by hand and the finished screen 1102 may be pulled by hand from between the rollers 1161, 1162 and/or one or more of the rollers in the system may be a driven roller, rotated by a motor appropriately connected to the roller for rotating it with desired speed and torque (e.g., but not limited to, motors 1164, 1165 driving rollers 1161, 1162). A suitable gearing system may be used interconnecting the motor and roller. In certain aspects one or more of the rolls and/or roller(s) are drive rolls and/or rollers which are rotated so that the mesh is moved through the system at a speed of between twenty and sixty feet per minute. In other particular aspects, the speed is about ten feet per minute. Any or all of the rolls and/or rollers may be coated with polytetrafluoroethylene and/or plastic, ceramic, or cermet material. By adjusting roll and/or roller rotation speed, e.g. with suitable brake and/or drag apparatus, tension can be maintained on the mesh or meshes to keep it or them sufficiently taut while moving through the system. Motor Systems M represent (schematically) rotating systems for the rolls and/or rollers. Any, some, or all of the systems M may be deleted.

Optionally, the finished screen 1102 may be wound onto a drum or roller 1179.

FIG. 2 shows a system 1100a like the system 1100 of FIG. 1 and the numerals indicate like components and similar glues may be used. The system 1100a does not have the gluing station 1120; but has a gluing apparatus for applying a desired pattern of glue to the coarse mesh 1104 that includes a glue reservoir/manifold 1125 from which glue is supplied to a plurality of glue nozzles 1126 (three shown). According to the present invention, a sufficient number of nozzles are used sufficiently spaced-apart and positioned to create a desired glue pattern of heated glue on the coarse mesh 1104. The resulting screen 1103 is like the screen 1102 and optional parts of the system 1100 may be used in the system 1100a. Other features of the system of FIG. 2 may be included in the system 1100a.

In other embodiments, a fine mesh is unwound from the roll 1111 and fine, finer, or coarse mesh or meshes are unwound from the rolls 1107 and 1109.

FIG. 3 shows one embodiment for a pressing station 1167, like the pressing station 1160, with rollers 1168 and 1169. A spring 1166 biased between a support member 1155 and a roller shaft mount 1164 yieldingly urges the roller 1168 against a multi-mesh combination 1105.

The meshes 1104, 1106, and 1108 may be any mesh or screen disclosed herein. The glue 1140 may be any suitable glue, including, but not limited to, polyethylene glues and hot melt glues at a suitable temperature for flowing to and from a reservoir/manifold and onto a mesh, e.g., but not limited to at about 250° F., between 250° F. and 400° F., or at other suitable temperatures for the particular glue being used.

FIGS. 5A and 5B show a pattern roller 1180 useful as the pattern roller 1130 of the system 1100 in FIG. 1. Raised portions 1181 on an exterior surface 1182 of the pattern roller 1180 form the desired pattern for applying glue to a mesh. The roller 1180 is solid with end shafts 1183 for mounting to suitable supports for rotation. Any pattern roller disclosed herein may be solid with end shafts like the end shafts 1183. Alternatively, recesses, holes, or indentations in one or both ends of the roller may be used to mount the roller to an appropriate shaft, mount, or support. Any of the pattern rollers disclosed herein, and any other roller used in systems according to the present invention, including, but not limited to systems as in FIGS. 1–3, may be coated with polytetrafluoroethylene.

FIGS. 6A and 6B show a roller 1180a like the roller 1180, but with a bore 1184 through the roller from one end to the other. Such a bored roller or "sleeve" may be installed on a common shaft or roller positioned as is the pattern roller 1130 in FIG. 1. With a plurality of such sleeves with different patterns thereon, changing the system to produce a different glue pattern is greatly facilitated. Also, a worn or degraded sleeve is easily removed and replaced. Such sleeves also facilitate clean-up of the system.

It is within the scope of this invention for the roller 1180 (and any roller according to the present invention) to include only the raised portions 1181 with no body or structure therebeneath nor between pattern components so that the portions 1181 and ends of the roller not only define a pattern but also form a perforated tube or sleeve. Such a tube or sleeve may be made from a piece of solid stock by machining and/or laser cutting. Any pattern for a roller described herein may be formed by grooves or recesses in a roller surface rather than by raised portions on a roller surface.

Figure 8:
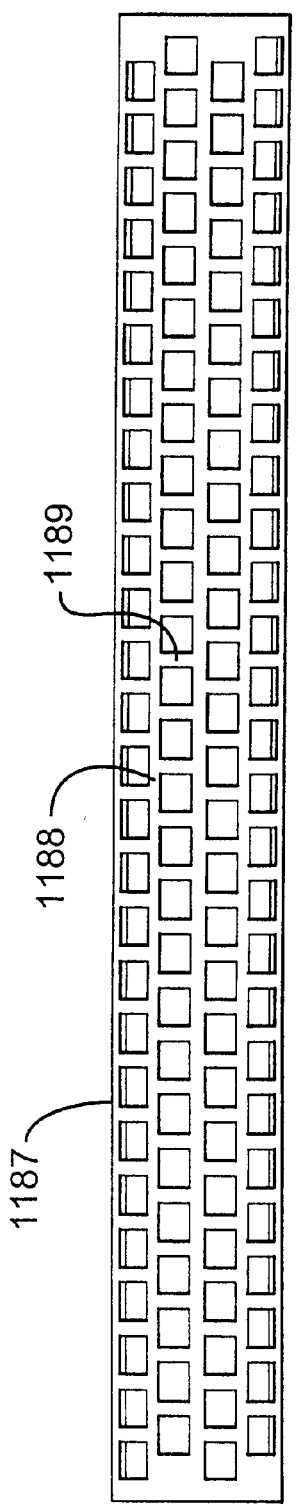

FIGS. 7 and 8 present pattern rollers with patterns or raised portions different from that of the patterns of the rollers of FIGS. 5B and 6B. The rollers of FIGS. 7 and 8 may have any of the options of the rollers of FIGS. 5B and 6B (including, but not limited to end shafts 1183 and bore 1184, or a perforated tube structure). A roller 1185 in FIG. 7 has raised lines 1186 that define a pattern across the roller. A roller 1187 in FIG. 8 has raised portions 1188 and 1189 that define a pattern across the roller.

Figure 9:
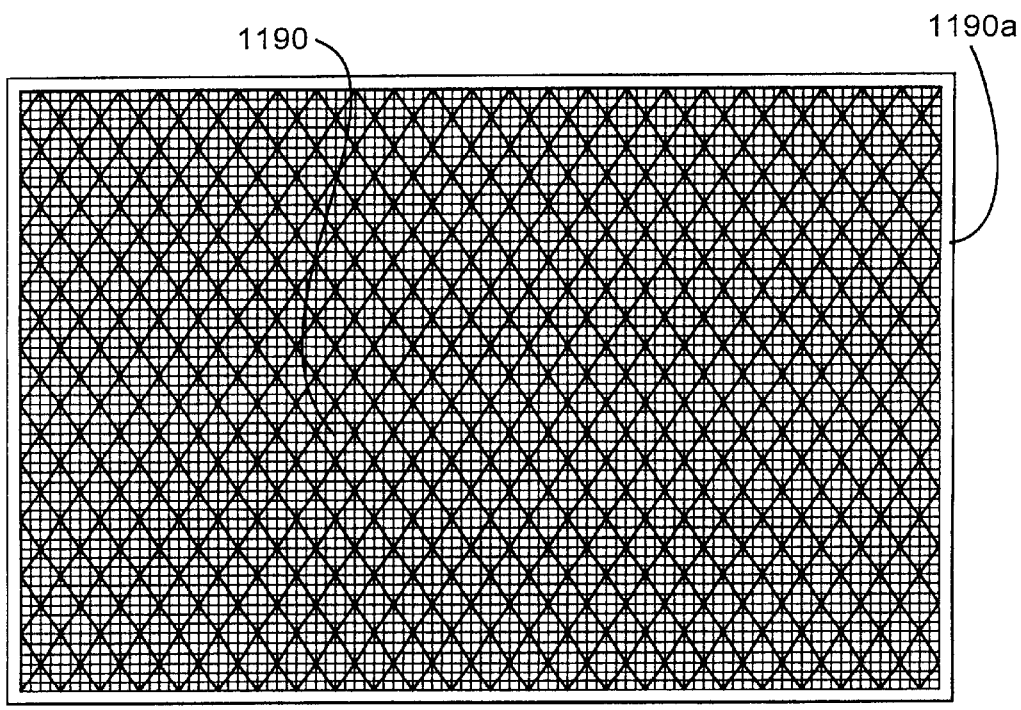
FIG. 9 is a top view of a screen according to the present invention.
Figure 10:
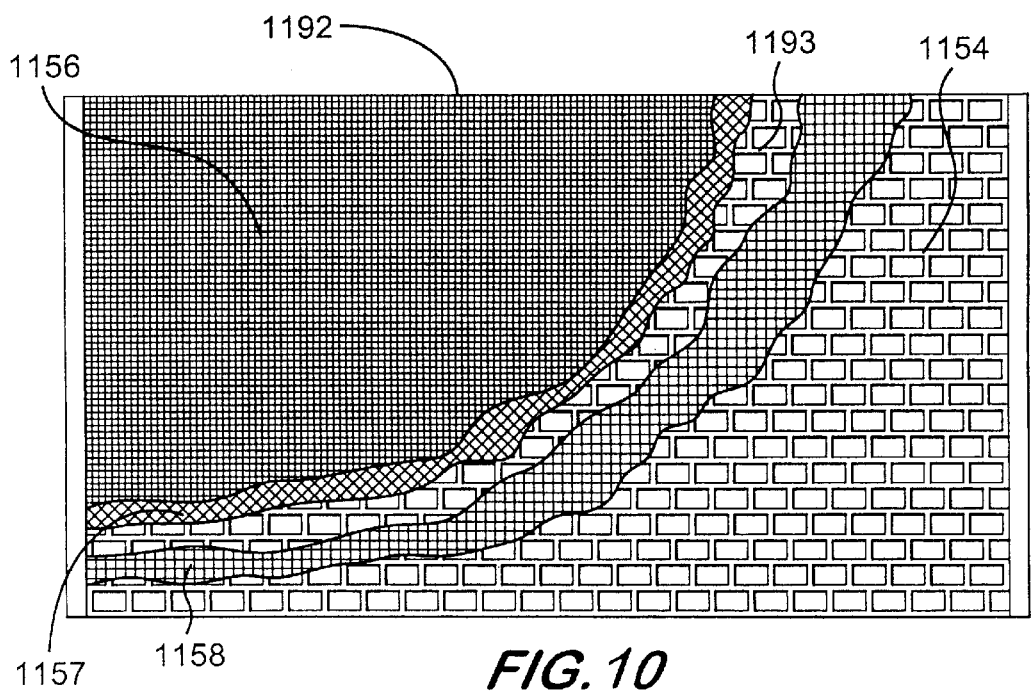
FIG. 10 is a top view, partially cut-away, of a screen according to the present invention.

FIG. 9 shows a screen 1190 produced with a system like the system 1100 (FIG. 1) using a roller like the roller 1185 (FIG. 7). FIG. 10 shows a screen 1192 with a glue layer 1193 according to the present invention produced with a system like the system 1100 (FIG. 1) using a roller like the roller 1187 (FIG. 8). The screen 1192 is like the screens disclosed in U.S. Pat. No. 4,575,421 (incorporated fully herein for all purposes), but made with a system according to the present invention and by a method according to the present invention. The screen 1192 has three layers of mesh or screening material 1156, 1157 and 1158 and a lower perforated plate 1154. Any of the layers of mesh may be deleted and the glue 1193 may be applied on top of any of the layers. In one aspect the plate 1154 is deleted. In one aspect the plate 1154 is deleted and any other support is used. The screen 1190 is like a screen disclosed in U.S. Pat. Des. 366,040 (incorporated fully herein for all purposes) and U.S. Pat. No. 5,971,159 (incorporated fully herein for all purposes). An optional frame 1190a is used around the screen 1190.

Figure 4A:
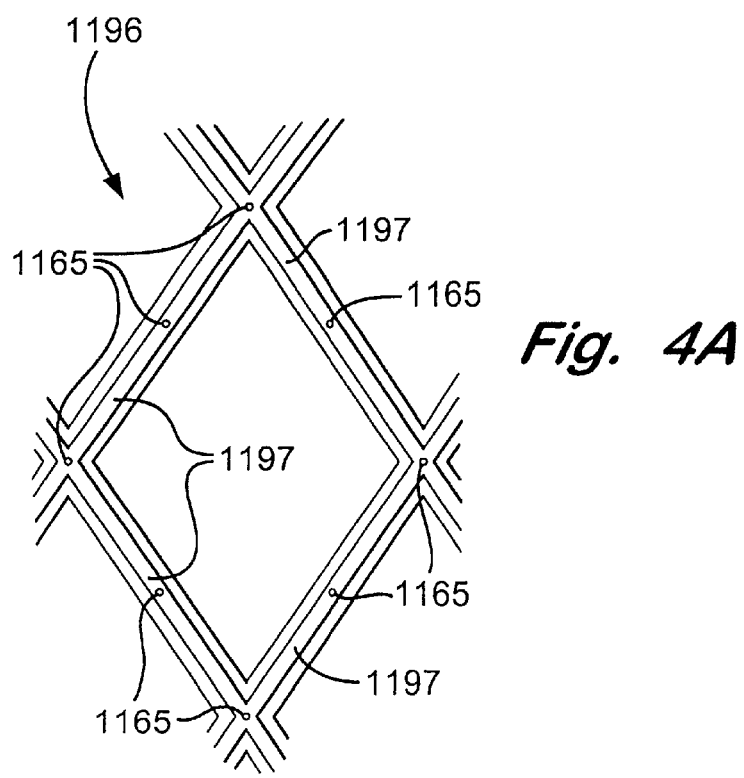
FIG. 4A is an enlarged front view of part of a pattern roller for apparatus as in FIG. 1.
Figure 4B:
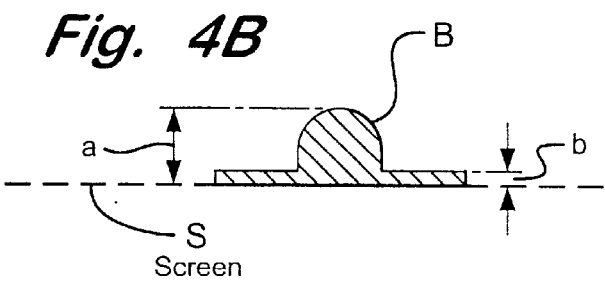
FIG. 4B shows a glue bead in cross-section according to the present invention.

FIG. 4A shows an enlargement of part of a pattern roller 1196 according to the present invention which is similar to the roller 1180 (FIG. 5B), but which has valleys, recesses or grooves 1197 in raised portions 1198 of the roller. Glue is received within the grooves 1197 so that a relatively higher or thicker level or bead of glue is applied to a mesh by the roller as compared to the layer or film of glue applied by a roller like the roller 1180. Any raised portion of any roller disclosed herein may include such a valley recess, or groove to increase the amount of glue applied on a mesh. In one aspect the grooves 1197 are between about one-thirtysecond to one-sixteenth inches deep and in one particular aspect are about one-sixteenth of an inch deep. Viewed on end in cross-section the grooves may be V or U shaped, square-shaped, trapezoidal, or semicircular. Optionally the roller 1196 has a bore through it (like the bore 1184, FIG. 6B) and holes are provided through the roller so that the roller's interior is in fluid communication with the grooves via the holes and glue can be flowed or pumped from the roller interior to the grooves to provide the glue for the pattern to be applied to the mesh. Alternatively, in embodiments in which the grooves are not used, holes are provided through the roller through the raised portions of a patterned surface. FIG. 4B shows a cross-section of one glue bead's B profile applied to a screen S with a pattern roller having grooves in raised portions of the pattern. The distance "a" is, in this embodiment, about one-sixteenth of an inch. Preferably the distance "b" is as thin as possible. It is within the scope of this invention to provide partial grooves or recesses in only a portion of the raised portions of a pattern rollers surface, e.g., but not limited to, only to the outer edges or only to the center, only to the edges and center, or only to certain spaced-apart portions on the roller to create a series of strips on the screen.

Figure 11:
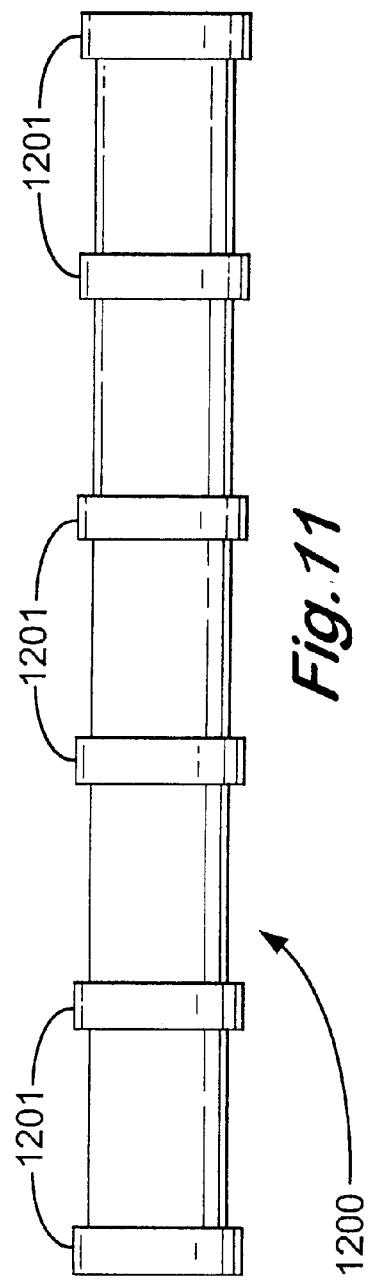
FIG. 11 is a side view of a pattern roller according to the present invention.

FIG. 11 shows a pattern roller 1200 according to the present invention which has raised pattern areas 1201 for forming a series of strips of glue on a screen or mesh or combination of layers thereof, including, but not limited to, a series of strips. It is within the scope of this invention to use an appropriately configured pattern roller to form any series of strips (like any series of strips disclosed herein for a screen or panel) on a screen or mesh with glue as described above. It is also within the scope of this invention for the areas 1201 or parts of them to have grooves around their entire surface (grooves or recesses as described above) or in part of the surfaces. Such a roller with or without grooves may also have holes as described above for introducing glue from the interior of the roller to the grooves and/or to the raised areas. By using a roller like the roller 1200 with only the two outer raised portions 1201, two spaced-apart sides can be created on screen or mesh. By turning a piece of such screen or mesh ninety degrees and feeding it again through a gluing system according to the present invention, two additional spaced-apart sides are created so that all four sides of the screen or mesh are glued.

The present invention, therefore, provides in some, but not necessarily all, embodiments a method for making a screen assembly for a vibratory separator, the method including placing at least two layers of screening material adjacent one another one on top of the other, introducing an amount of glue to the at least two layers of screening material for adhering at least portions of them together, the amount of glue introduced to the at least two layers of screening material from a roller with a patterned surface thereon so that the amount of glue is introduced to the at least two layers of screening material in a pattern corresponding to a pattern of the patterned surface of the roller, the roller rotatably mounted adjacent the screening material. Such a method may include one or some (in any possible combination) of the following: wherein the at least two layers of screening material is three layers of screening material; wherein the at least two layers of screening material includes at least a first layer and a second layer, the first layer comprising coarse mesh and the second layer comprising fine mesh or vice versa; wherein the at least two layers of screening material comprises at least a first layer and a second layer, the first layer wound onto a first roll and the second layer wound onto a second roll, and the method also including unrolling the first layer from the first roll and unrolling the second layer from the second roll to place the layers adjacent each other; wherein prior to placing the layers adjacent each other the amount of glue is applied on the first layer; wherein the amount of glue is applied after the at least two layers of screening material are adjacent each other onto a topmost layer of the at least two layers; wherein the patterned surface comprises raised portions on the roller; wherein the raised portions have a groove therein for holding glue to be applied to the screening material in a pattern with a raised bead portion; wherein the roller with the patterned surface is a first roller and a second roller rotatably mounted adjacent the first roller receives glue from a glue reservoir and applies the glue onto the first roller; wherein a third roller is rotatably mounted adjacent the second roller so that a pond of glue is maintained between the second roller and the third roller and glue from the pond of glue is moved by the second roller to the first roller; wherein glue is flowed directly onto the first roller from a reservoir of glue; wherein the patterned surface comprises raised portions on the roller and the raised portions have a groove therein for holding glue to be applied to the screening material and wherein glue is flowed to an interior of the first roller from a reservoir of glue and wherein the interior of the roller is in fluid communication with the grooves via a series of holes so that glue is movable from the roller's interior, to the grooves, to the patterned surface on the roller; the method also including pressing together the at least two layers of screening material and the amount of glue; wherein the at least two layers are pressed together between two opposed rotatable rollers; wherein the glue is a hot melt glue and the method includes cooling the glue after it is introduced to the at least two layers of screening material; wherein at least one of the two opposed rotatable rollers is a driven roller; wherein coolant fluid is pumped through at least one of the two opposed rotating rollers to cool the glue; wherein the at least two layers of screening material include at least one first layer which is wound onto a first roll and unwound therefrom and which is supported on a plurality of rotatable rollers as it is unwound; wherein the roller is a bored roller which has a bore therethrough so that the bored roller is emplaceable over a common roller; wherein the roller with the patterned surface is a first roller, and at least a second roller is provided with a second patterned surface, the patterned surface of the first roller different from the patterned surface of the second roller; wherein each of the first roller and the at least a second roller have a bore therethrough so that either roller is emplaceable on a common shaft to apply its pattern to the screening material; wherein the first roll and the second roll are driven rolls; wherein the roller with a patterned surface is a driven roller; wherein the second roller is a driven roller; wherein the third roller is a driven roller; the method also including heating the amount or pond of glue or glue in the reservoir; wherein the first roll and the second roll are heated rolls; wherein the roller with a patterned surface is a heated roller; wherein the second roller is a heated roller; wherein the third roller is a heated roller; wherein the pattern extends over substantially the entire surface of the layers of screening material; wherein the raised portions with grooves are positioned on the pattern roller so that raised bead portions extend along spaced apart outer edges of the screen assembly. A screen assembly made by any method according to the present invention. A glue pattern produced by a system according to the present invention may be any desired pattern, including but not limited to, any pattern of any glue layer or of any panel or frame or series of strips disclosed herein and a pattern roller with a corresponding pattern thereon is used to produce such a pattern.

Figure 12:
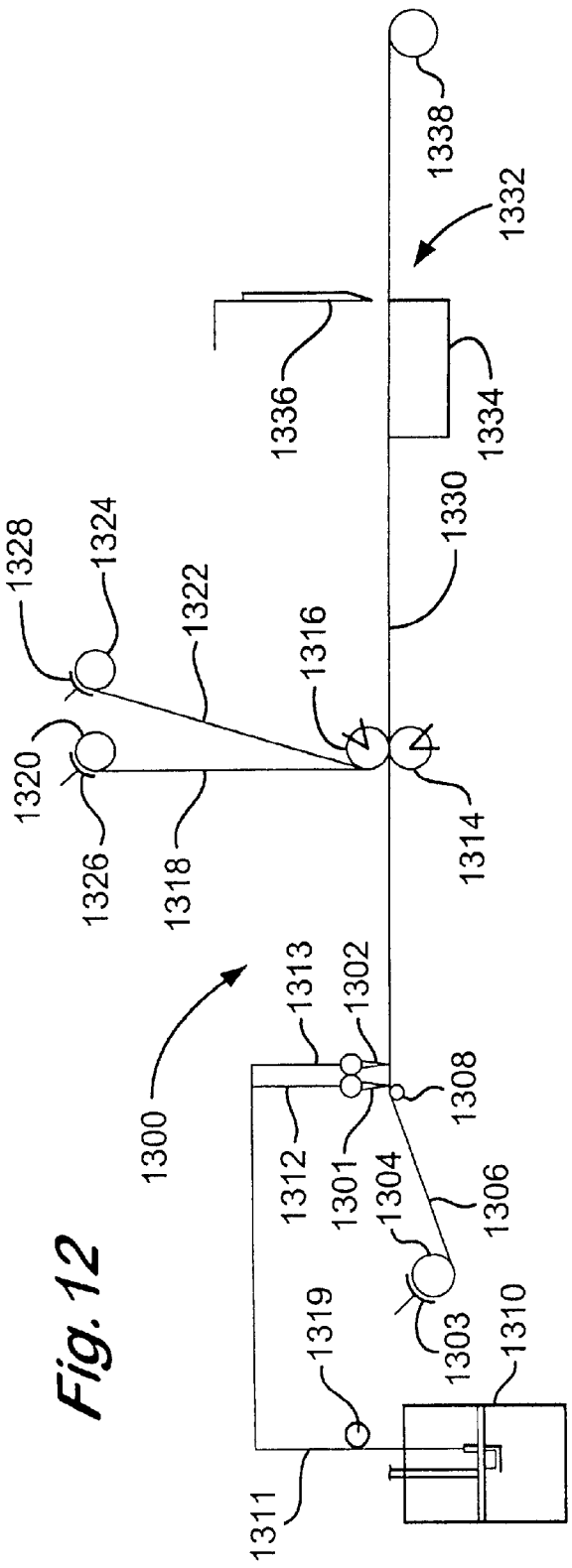
FIG. 12 is a side schematic view of a system according to the present invention.

FIG. 12 shows a system 1300 according to the present invention for applying glue in a desired pattern to a screen or screens (or mesh or meshes) and can be used to produce any screen disclosed herein that employs glue or adhesive between two or more layers of screen(s) and/or mesh(es).

Hot glue for application to screen(s) or mesh(es) or combination thereof is supplied to nozzles 1301, 1302 from a glue apparatus 1310 through lines 1311, 1312, and 1313. Either of the nozzles may be deleted; or, as in the system of FIG. 2, more than two nozzles may be used. The line 1311 may be a heated line or a heated hose heated by optional heater apparatus 1319. Any suitable known glue system may be used in systems according to the present invention, including but not limited to hot glue systems which heat glue and then pump it to a flow line. In one particular aspect BulkMeter Applicators Model 5530, 5540, or 5506 commercially available from the Nordson Corporation of Amherst, Ohio may be used in systems according to the present invention (e.g. for the apparatus 1310 in the system of FIG. 12).

From a rotating roll 1304 a sheet of screen or mesh 1306 is unwound from the roll 1304 and moved over an idler roller 1308 to a position beneath the nozzles 1301, 1302 (or only one of them when one of them is deleted). A brake 1303 provides tension on the screen or mesh 1306 as it is pulled from the roll 1304. In certain aspects a roll of woven wire (screen or mesh) between e.g. 100 to 300 feet in length is rolled from the roll 1304.

The screen or mesh 1306 with a glue pattern deposited thereon (any glue disclosed herein) moves between a rotating stationary (with respect to vertical position) roller 1314 and rotating adjustable (with respect to vertical position) roller 1316. In certain aspects it is preferred that the rollers 1308, 1314 are as close together as possible. Any roller in the system or roll can be a "driven" roller or roll, e.g. powered by a motor with appropriate gearing, shafts, interconnections, etc., to pull the woven wire (screen or mesh) from the roll 1304. In one particular aspect the roll 1338 is a driven roll that pulls the woven wire from the roll 1304. The driven roll 1304 (or other driven roll or roller) can be rotated continuously as glue is deposited on the screen or mesh; or it can be drivingly rotated at intervals so that a desired portion of a layer of wire mesh is positioned beneath the nozzle(s) for glue pattern deposition. Following application of the desired glue pattern to the portion of the layer, the roll is again activated to remove the portion with the glue pattern and to position a new un-treated portion beneath the nozzle(s).

A second screen or mesh sheet 1318 unwound from a rotating roll 1320 and, optionally, a third screen or mesh sheet 1322 unwound from a rotating roll 1324, are also fed between the rollers 1314, 1316 between which all the sheets are pressed together. Brakes 1326, 1328 provide tension as desired on the rolls 1320, 1324, respectively. Pressure on the combination of sheets may be adjusted by adjusting the vertical position of the adjustable roller 1316. It is within the scope of this invention to make a screen with any desired number of layers, or sheets of screening material (screen and/or mesh), including, but not limited to a final screen product with one, two, three, four, five or more layers.

In certain aspects the adjustable roller 1316 is positioned so that the sheets moving between the rollers 1314, 1316 are bound together and part of the sheets are encapsulated in glue of the glue pattern. Either or both of the rollers 1314, 1316 can be a driven roller (e.g. driven with a motor M as in FIG. 1) to pull the various sheets between the rollers from their respective rolls. The rollers may act as heat sinks removing heat from the glue and/or cooling fluid may be circulated through one or both rollers to cool the glue.

Optionally a screen and/or mesh combination 1330 exiting from between the rollers 1314, 1316 may be cut to length as desired with a shear apparatus 1332 including a support 1334 and a shear device 1336; or the combination 1330 may be wound onto a roll 1338.

In one particular aspect the sheet 1306 is a layer of relatively coarse wire mesh (and, in certain embodiments, may be any coarse wire mesh disclosed herein); the sheet 1318 is a layer of medium wire mesh (and may be any medium wire mesh, e.g., but not limited, between 20 mesh and 250 mesh disclosed herein); and the sheet 1322 is a layer of fine wire mesh (and may be any fine wire mesh disclosed herein).

Figure 13A:
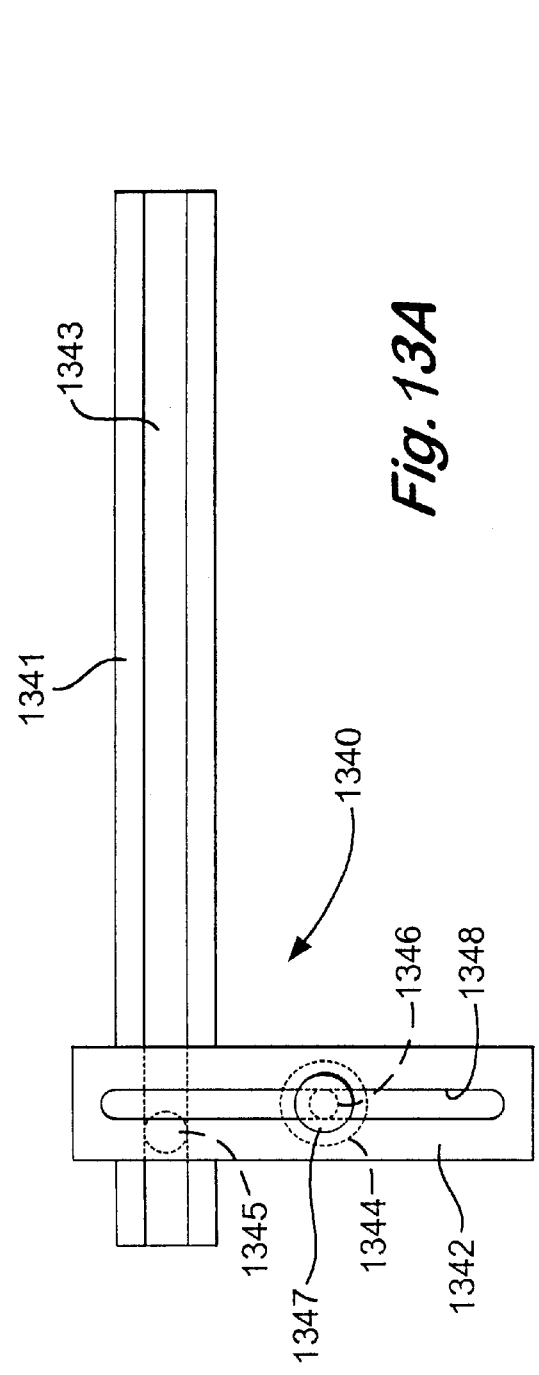
FIG. 13A is a top schematic view of part of a system as in FIG. 12.

Any suitable known movement mechanism may be used to move the nozzle or nozzles above a layer of screen or mesh. One movement mechanism 1340 is shown schematically in FIG. 13A and includes a first bar 1341 at right angles to a second bar 1342 on which is movably mounted a glue nozzle 1344. The second bar 1342 has a finger 1345 that projects down into a guide channel 1343 of the first bar 1341. As the second bar 1342 moves with respect to the first bar 1341 the finger 1345 moves in the guide channel 1343 to guide the movement of the second bar 1342. The glue nozzle 1344 moves along the second bar 1342, e.g. a shaft 1346 projecting down from a knob 1347 moves in an elongated opening 1348 to guide movement of the glue nozzle 1344 with respect to the second bar 1342. Appropriate movement of the second bar 1342 with respect to the first bar 1341 and simultaneously of the glue nozzle 1344 with respect to the second bar 1342 makes possible the application of a glue bead in a desired pattern on a screen or mesh below the nozzle 1344. One, two, three, four or more glue nozzles may be movably mounted on the second bar; or a plurality of glue nozzles each with its own movement mechanism may be used. Alternatively, and for any embodiment disclosed herein, the layer or layers of screening material may be moved below fixed nozzle(s) to produce a desired glue pattern thereon. For example a portion of a roll of mesh to have a glue pattern deposited thereon is placed on a movable and indexable table or other suitable support with a nozzle or nozzles mounted thereabove.

Figure 13B:
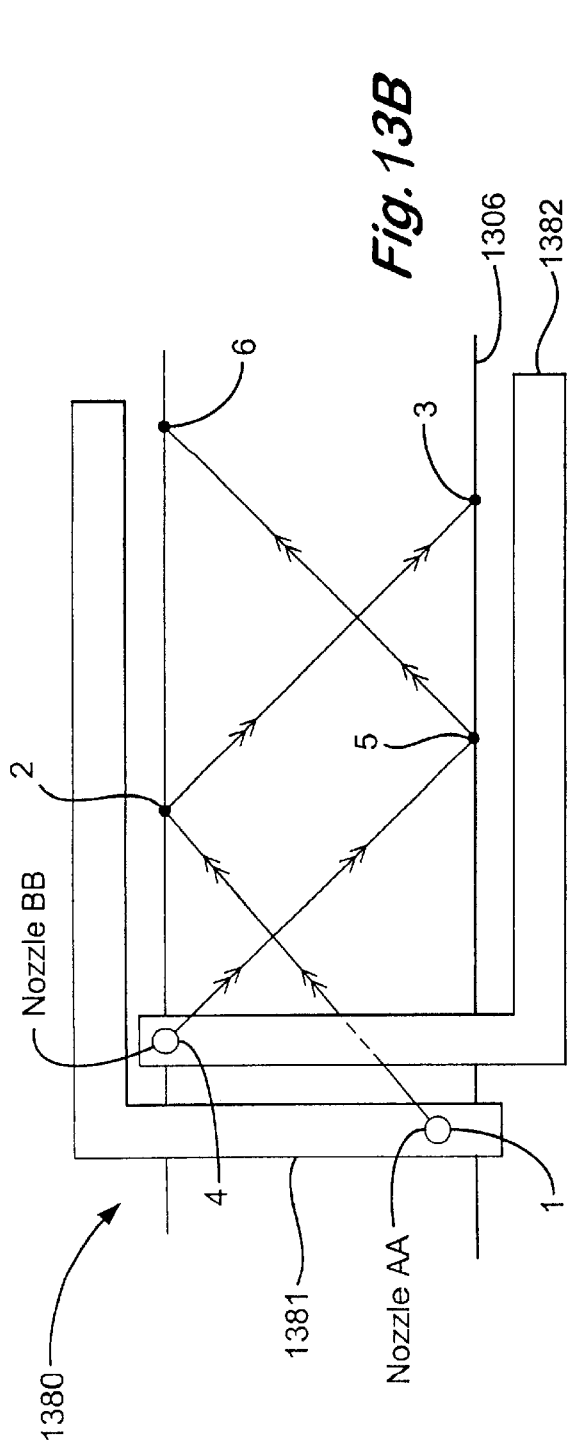
FIG. 13B is a top schematic view of a system according to the present invention.

FIG. 13B shows a system 1380 according to the present invention with two nozzle movement mechanisms 1381, 1832 (like the mechanism of FIG. 13A) each with a nozzle AA and a nozzle BB respectively. In one method according to the present invention, nozzle AA is moved from the indicated position 1 to a new position 2, depositing a first glue bead on the screen or mesh 1306 (like that in FIG. 12) along a path from position 1 to position 2. The nozzle BB is moved (and may be moved before the nozzle AA is moved) from its initial position 4 to a new position 5, depositing as it moves a glue bead on the screen or mesh 1306 along the path from position 4 to position 5. The screen or mesh 1306 is then moved a predetermined increment (to the right or to the left as viewed in FIG. 13B) and nozzle AA is moved back to position 1 (depositing a new glue bead on the screen or mesh as it moves, the new glue bead spaced-apart from the first glue bead) and, similarly, the nozzle BB moves back to position 4 depositing a corresponding glue bead. Alternatively, both nozzles may move on to a subsequent position (instead of moving back to positions 1 and 4, respectively); position 3 for nozzle AA and position 6 for nozzle BB. It is within the scope of this invention for the nozzles to then move back to their initial positions following a movement or indexing of the screen or mesh, depositing a new glue bead when traversing the screen or mesh in the reverse direction (or not depositing a glue bead). The position 1 to 2 to 3 (nozzle AA) and position 4 to 5 to 6 (nozzle BB) movements can then be repeated. Alternatively only one of the nozzles may be used, moving to a second position and, optionally, on to a third position, and, optionally, then back to the second and then the first position. Although the nozzle paths shown in FIG. 13B are substantially straight it is within the scope of this invention for either or both paths to be curved, zig zag, or wavy as viewed from above.

Typically a deposited glue bead has a width as viewed from above of between 3/64ths and 3/32nds of an inch, and, in one particular aspect this width is about 1/16 inch. In certain aspects the distance of a glue nozzle above a layer of screen or mesh is between 3/8 inch to 5/8 inch and the nozzle (or nozzles) are moved at a rate of 4 to 6 feet per minute (or the layer of screen or mesh is moved below a stationary nozzle or nozzles at this rate).

Figure 14:
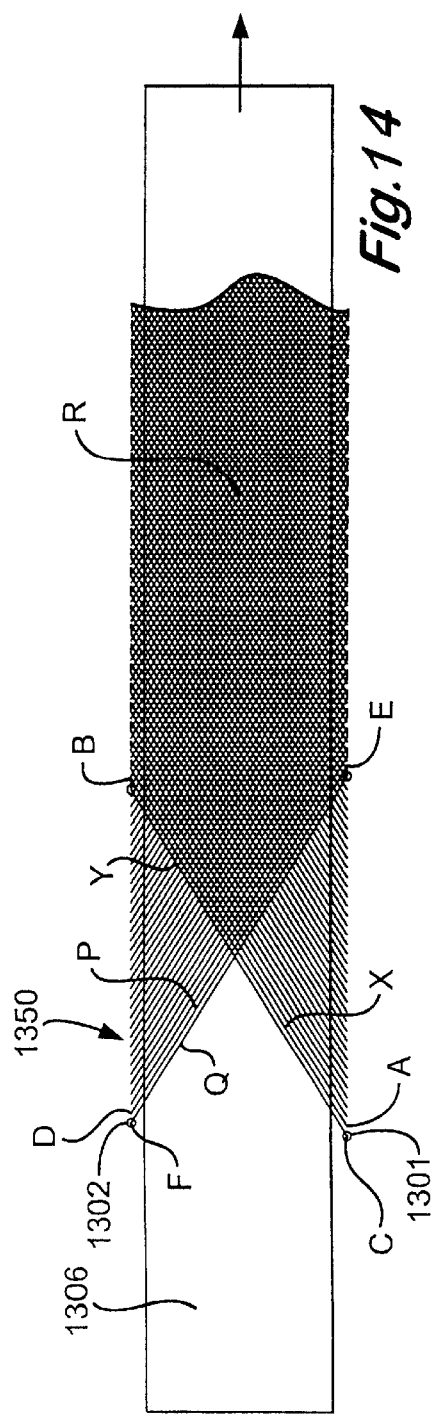
FIG. 14 is a top schematic view of a system according to the present invention.

FIG. 14 shows a system 1350 according to the present invention like the system of FIG. 12 in which the nozzles 1301, 1302 are initially positioned on opposite sides of a stationary portion of a layer of screen or mesh 1306. Nozzle 1301 moves from a position A to a position B laying down a glue bead X and then reverses direction and moves from position B to position C laying down a glue bead Y. Simultaneously the nozzle 1302 moves from a position D to a position E laying down a glue bead P and then reverses direction and moves to a position F laying down a glue bead Q. As these movements of the nozzles are repeated a pattern R of glue is deposited on the screen or mesh 1306. When the nozzles have covered the desired portion of the layer of screen or mesh with the desired pattern, the layer is moved beneath the nozzles so that they are then positioned above a new layer portion to which the pattern is to be applied. Once the new portion is correctly positioned, the nozzles begin applying the glue pattern as before. Alternatively, the screen or mesh also moves below the nozzles as the glue is being dispensed.

Figure 15:
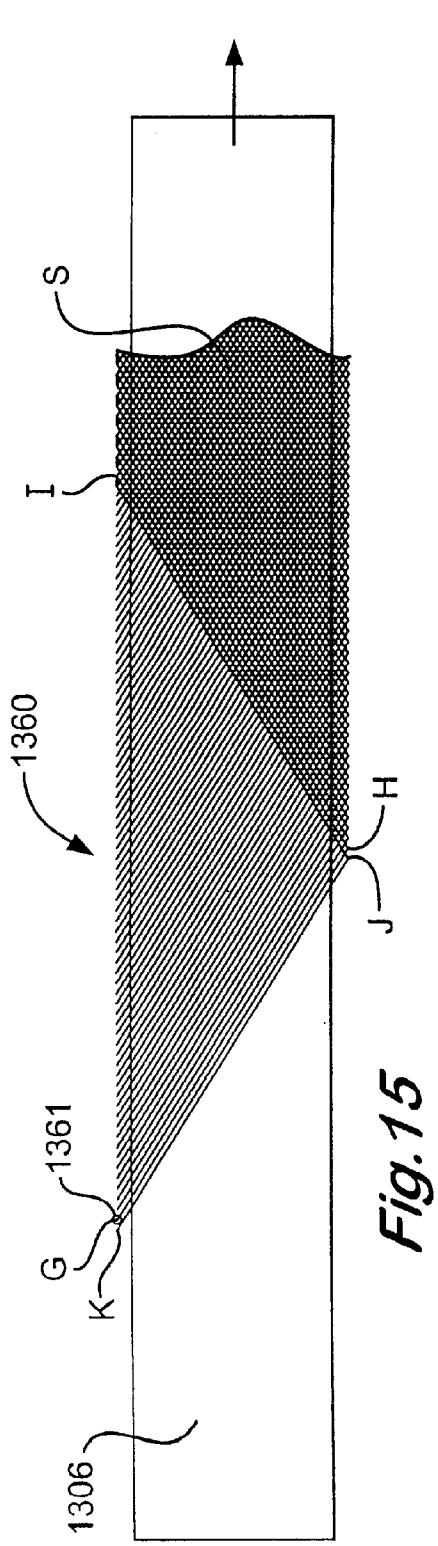
FIG. 15 is a top schematic view of a system according to the present invention.

FIG. 15 shows a system 1360 according to the present invention like the system of FIG. 12 with a single glue nozzle 1361 that dispenses a glue bead onto the screen or mesh 1306 and moves from a position G, to a position H, then to a position I, to a position J, and then to a position K. By repeating this cycle of movement a pattern S of glue is applied to the screen or mesh 1306. When the desired pattern has been applied to a portion of the screen or mesh 1306, the glue flow is (optionally) shut-off, the screen or mesh 1306 is moved beneath the nozzle 1361 so that glue may be applied to another portion of the screen or mesh 1306. Alternatively, the layer of screen or mesh 1306 also is moved beneath the nozzle 1361 as glue is being applied thereto; or, in another aspect, following nozzle movement (e.g. from points G to H to I) the screen or mesh is moved (e.g. indexed a desired distance) below the nozzle and then the nozzle is moved in a reverse path (e.g. from points I to J to K).

Figure 16:
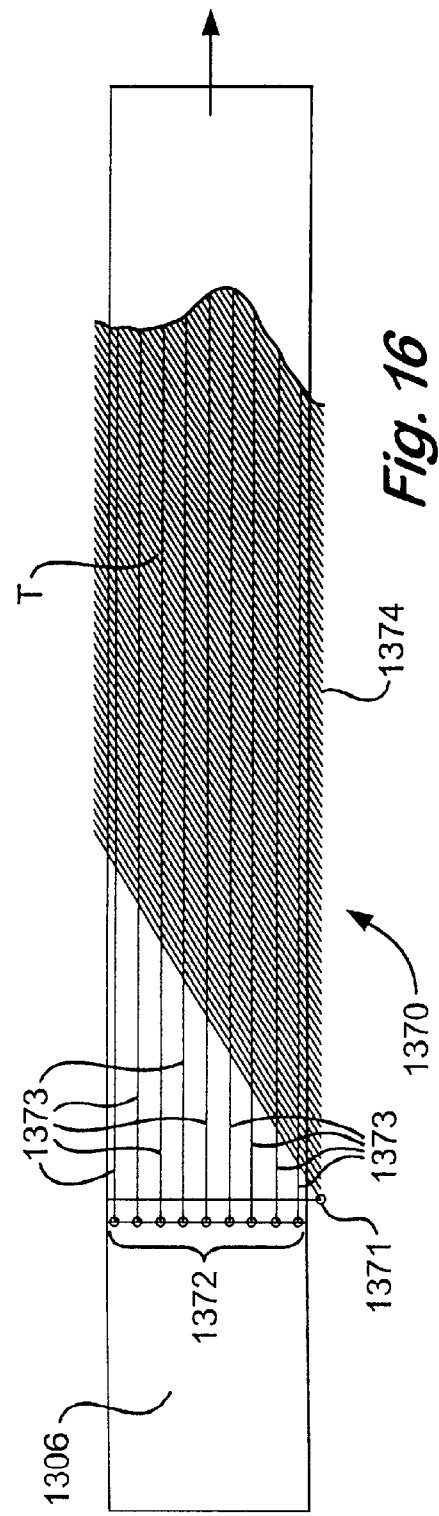
FIG. 16 is a top schematic view of a system according to the present invention.
Figure 17A:
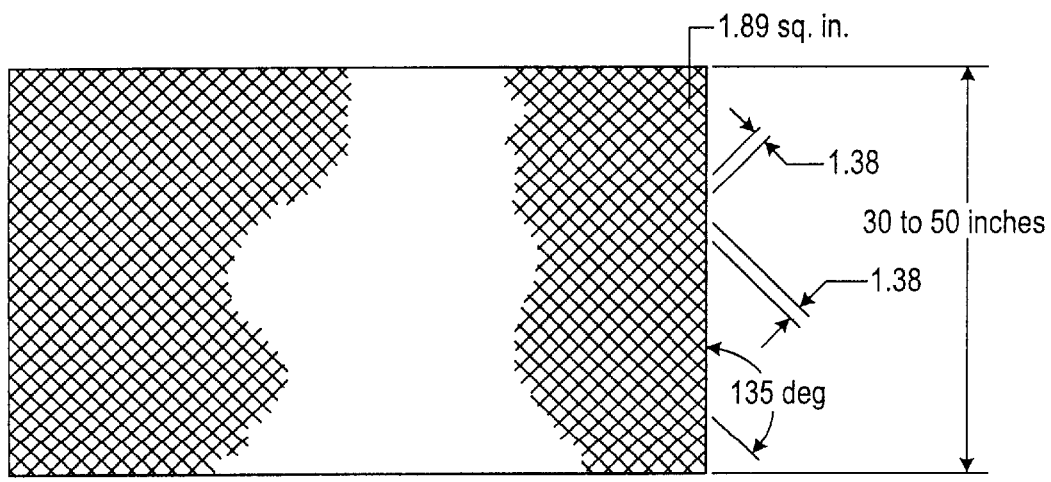
FIGS. 17A–17D are top views of glue patterns applied by a system according to the present invention.
Figure 17B:
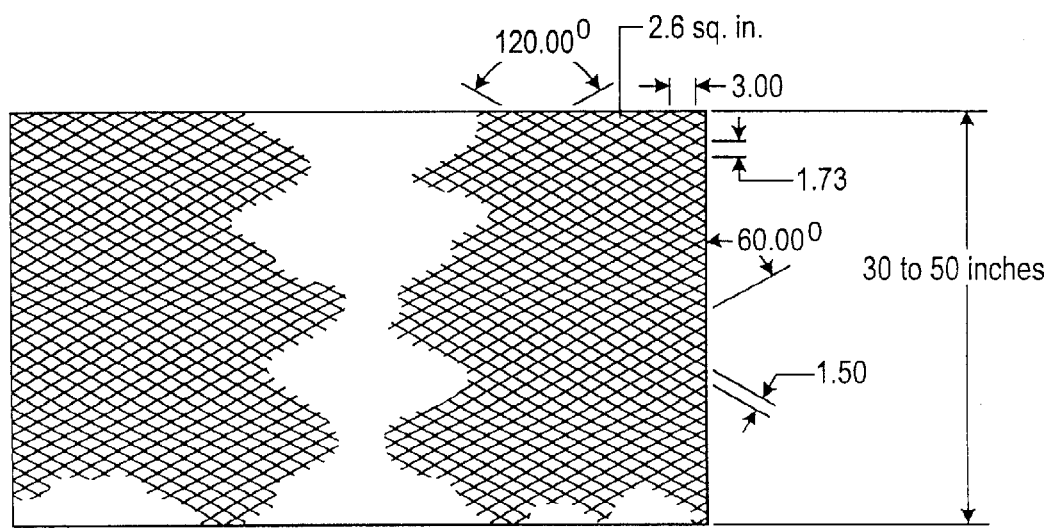
Figure 17C:
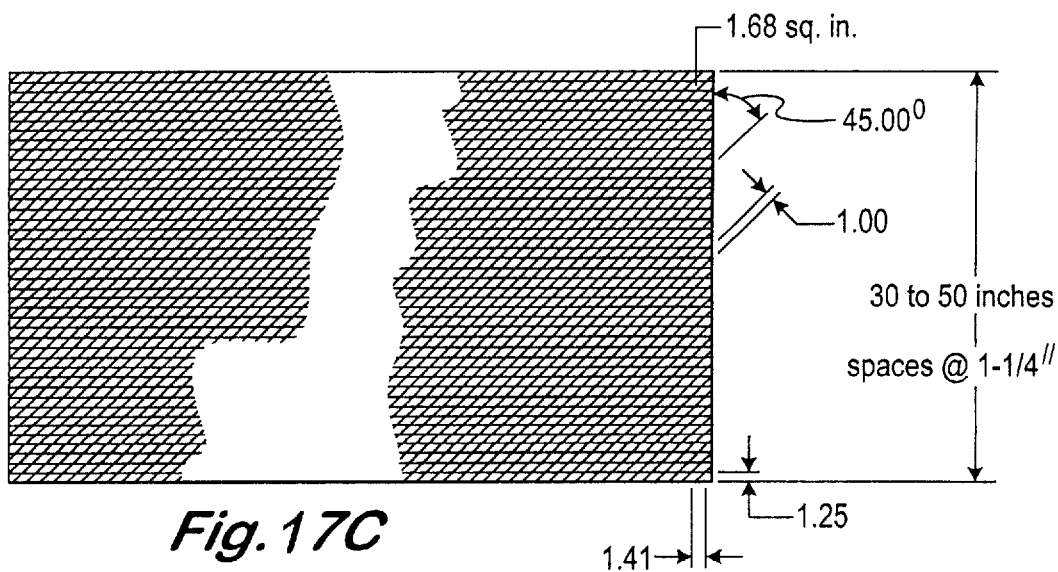
Figure 17D:
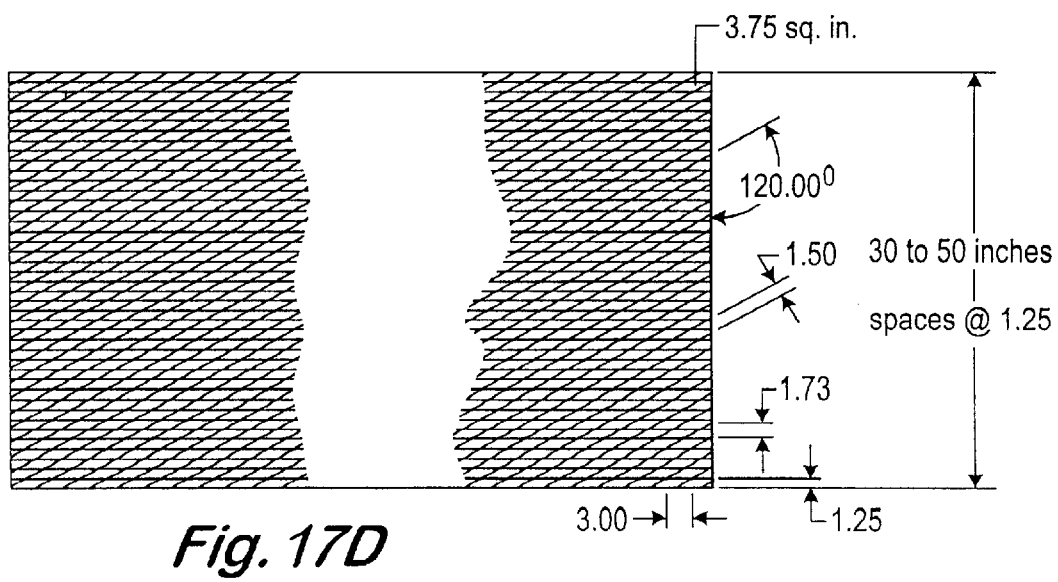

FIG. 16 shows a system 1370 according to the present invention like the system of FIG. 12 with a bank of a plurality of glue nozzles 1372 and a glue nozzle 1371. The bank of nozzles 1372 applies a plurality of glue beads 1373 to the screen or mesh 1306. The nozzle 1371 moves above the screen or mesh 1306 to apply a plurality of glue beads 1374, producing a pattern T of glue on the screen or mesh 1306. Either the bank of nozzles is moved with respect to the layer of screen or mesh 1306, or the layer is moved below the bank of nozzles, or both. It is also possible to move the entire bank of nozzles at an angle to the direction of movement of the layer of screen or mesh 1306. Also, a bank of nozzles may be used on the side of the layer 1306 instead of a single nozzle like the nozzle 1371.

FIGS. 17A–17D show possible glue patterns that may be applied by systems according to the present invention (including, but not limited to, systems as in FIG. 13, FIG. 13B and FIGS. 14–16). These patterns can be achieved by appropriate control of rate of movement of the screen or mesh and/or by the rate and/or direction of travel of the nozzle(s). In FIGS. 17A–17D, angle measurements are in degrees (either "°" or "deg"), length measurements are in inches ("inches" or "in" or a number, e.g. FIG. 17A "1.38" is 1.38 inches) and area measurements ("sq. in.") are in square inches. It is also within the scope of this invention: to substitute any patterning roller described herein for any bank of nozzles (e.g. but not limited to the bank of nozzles in the system 1370); to substitute any patterning roller described herein for any nozzle in any system in FIGS. 12–16; and to use a roller to deposit any glue bead deposited by any nozzle in any system in FIGS. 12–16.

As with other systems described herein, the cooling of hot glue deposited by a nozzle or nozzles can be effected by applying moisture to the glue and/or by the use of one or more fans or coolers and/or by circulating cooling fluid through one or more rollers and/or cooled rollers that contact and/or are adjacent hot glue.

The present invention, therefore, provides in some, but not necessarily all, embodiments a method for making a screen assembly for a vibratory separator, the method including placing a first layer of screening material below a glue application apparatus, and applying with the glue apparatus an amount of glue in a pattern to a portion of the first layer of screening material. Such a method may have one or some (in any possible combination) of the following: wherein the first layer of screening material comprises coarse mesh; wherein the first layer of screening material is removably wound onto a first rotatable roll, the method including unrolling the first layer of screening material from the first roll and positioning a portion of the first layer beneath the glue application apparatus; wherein a second layer of screening material is removably wound onto a second roll, the method further including unrolling part of the second layer from the second roll and positioning the part of the second layer adjacent part of the first layer to which glue has been applied, and moving the part of the second layer and the part of the first layer between opposed rotatable spaced-apart rollers to press together the part of the second layer and the part of the first layer to form a pressed together layer of first and second layers of screening material; continuously moving the second layer and the first layer between the opposed spaced-apart rollers producing a continuous sheet of pressed together screening materials; cutting the continuous sheet of pressed together screening material to form sub-sheets of pressed together screening material; wherein the amount of glue is heated and the method further including cooling glue in the continuous sheet of pressed together screening material, and winding the continuous sheet of pressed together screening material onto a third roll; wherein the amount of glue is heated and the method further including cooling glue in the pressed together layer; unrolling part of the third layer from the third roll and positioning the part of the third layer adjacent part of the first and second layers, and moving the part of the third layer and the parts of the first and second layers between the opposed rotatable spaced-apart rollers to press them together to form a pressed-together layer of first, second and third layers of screening material; continuously moving the layers between the opposed spaced-apart rollers producing a continuous sheet of pressed-together screening materials; cutting the continuous sheet of pressed-together screening material to form sub-sheets of pressed-together screening material; wherein the amount of glue is heated and the method further including cooling glue in the continuous sheet of pressed-together screening material, and winding the continuous sheet of pressed-together screening material onto a third roll; wherein the amount of glue is heated and the method further including cooling glue in the pressed-together layer; wherein the glue application apparatus includes at least one glue dispensing nozzle and apparatus for providing hot glue to the at least one glue dispensing nozzle for application in the pattern onto the first layer of screening material; wherein the at least one glue dispensing nozzle is a plurality of spaced-apart glue dispensing nozzles; wherein the glue dispensing apparatus has at least one glue dispensing nozzle and the method further including moving the at least one glue dispensing nozzle above the first layer of screening material to form the pattern of glue thereon; wherein the glue dispensing apparatus has at least one glue dispensing nozzle and the method further including moving the first layer of screening material beneath the at least one glue dispensing nozzle to form the pattern of glue on the first layer of screening material; wherein the glue dispensing apparatus has at least one glue dispensing nozzle and the method further including moving the at least one glue dispensing nozzle above the first layer of screening material to form the pattern of glue thereon, and moving the first layer of screening material beneath the at least one glue dispensing nozzle to form the pattern of glue on the first layer of screening material; the first layer is coarse mesh, and the second layer is medium mesh; the first layer is coarse, the second layer is medium mesh, and the third layer is fine mesh; wherein the pattern forms a series of a plurality of adjacent similarly-shaped repeating closed shaped with an open central area and glue bead sides, said series extending across substantially all the portion of the first layer of screening material to which glue is applied in the pattern; wherein each closed shape comprises a four-sided figure as viewed from above; wherein the four-sided figure is a parallelogram; wherein the parallelogram has interior angles of about 60°, 60°, 120° and 120°; wherein the four-sided figure is a rectangle; wherein the four-sided figure is a square; wherein at least one of the two opposed rotatable spaced-apart rollers is a driven roller; and/or heating the amount of glue.

The present invention, therefore, provides in at least certain aspects, a screen assembly made by any of the methods described above according to the present invention.

Figure 18A:
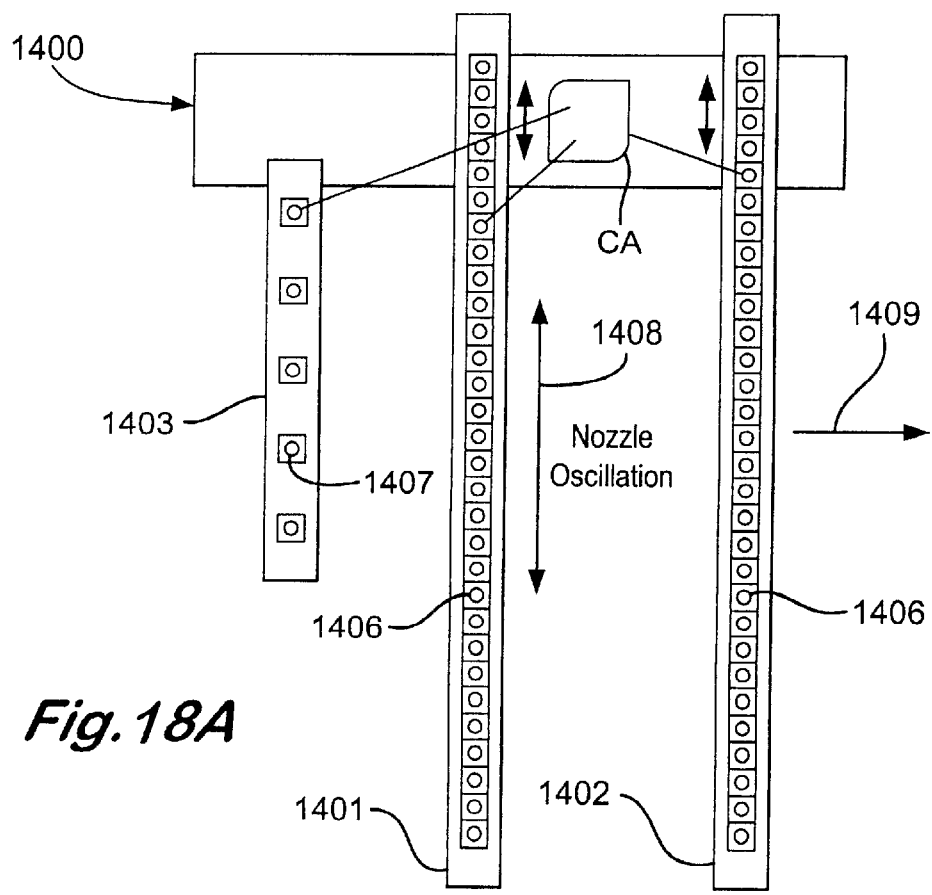
FIG. 18A is a top schematic view of a glue applicator used to produce a screen assembly according to the present invention.

FIG. 18A shows a glue applicator apparatus 1400 which has a main housing with appropriate controls, flow lines, etc. as are well known in the art and two movable nozzle manifolds 1401, 1402 that are movably connected to the apparatus 1400 with any known suitable manifold movement apparatus. A third nozzle manifold 1403 is secured immovably with respect to the apparatus 1400. In one particular aspect a scotch yoke cam arrangement may be used to move the manifolds 1401, 1402 with respect to the apparatus 1400.

As shown by the arrow 1408 in FIG. 18A the manifolds 1401, 1402 oscillate at approximately a right angle to the apparatus 1400, although it is within the scope of this invention for them to be positioned so that they oscillate at any desired angle with respect to the apparatus 1400 and with respect to screening material beneath them. An arrow 1409 indicates the direction of travel of screening material (including but not limited to any screening material disclosed herein) beneath the nozzles 1406 of the manifold 1401, nozzles 1405 of the manifold 1402, and nozzles 1407 of the manifold 1403. Any number of nozzles may be used on any of the manifolds and any number of manifolds may be used, stationary or movable with respect to the apparatus 1400. The manifold 1403 may be deleted as may be either or both of the manifolds 1401, 1402. The position of the nozzles 1407 may be adjusted with respect to the manifold 1403 and moved as desired prior to glue application. Once positioned they are releasably fixed in place with any suitable fixing apparatus and/or fastener(s).

In certain particular aspects, an apparatus 1400 has movable manifolds whose oscillation rate is adjustable from 7 to 200 oscillations per minute and whose oscillation width is adjustable up to 1.75 inches. The screening material, in certain aspects, is movable beneath the glue nozzles at between 5 and 30 feet per minute and the nozzles of the movable manifolds are on 1.65 inch centers (i.e., nozzle centers are 1.65 inches apart from each other). In certain aspects the tips of the nozzles (on all manifolds) are adjustable up and down so that nozzle-tip-to-screening material distance is adjustable between one-quarter inch to one-inch. The spacing of the nozzles of the manifold 1403 can be adjusted as desired. Control apparatus CA can automatically or as desired provide glue flow to or shut-off glue flow to any nozzle or any number of selected nozzles, e.g., but not limited to, every other nozzle. Also, either of the movable manifolds may be used in a stationary mode while the other oscillates. In certain particular aspects the glue beads for the screens of FIGS. 18B–19D are as previously described herein or they are between 0.012 to 0.05 square inches (in cross-sectional area) when applied to screening material moving beneath the glue nozzles at between five to fifteen feet per minute or between 0.007 to 0.05 square inches with material moving between fifteen to thirty feet per minute. Particular glues that may be used for the glue beads are known PUR glue and known EVA glue.

Figure 18B:
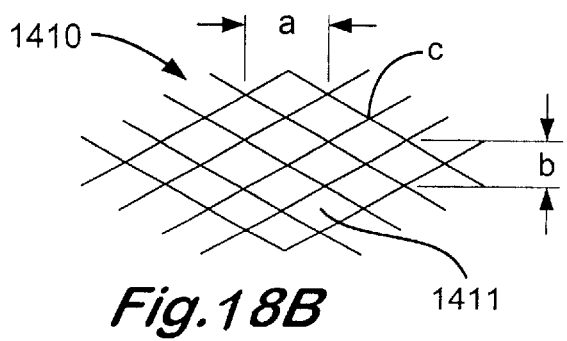
FIGS. 18B and 18C are top views of glue patterns according to the present invention.

FIG. 18B shows a glue bead pattern 1410 applied by an apparatus as in FIG. 18A (or by one of the apparatuses previously discussed above). The lines in FIG. 18B indicate the center of linear glue beads and any glue bead disclosed herein may be employed. The screen with such linear glue beads may be sheared by shearing down the length of the glue bead either manually with a shearing device, knife or scissors or with an appropriate shearing apparatus. The distance "a" is the distance between adjacent horizontal vertices (as viewed in FIG. 18B) of the plurality of parallelograms 1411 and the distance "b" is the distance between adjacent vertical vertices (as viewed in FIG. 18B) of the parallelograms 1411. Letter "c" indicates a radius of curvature for a curve portion indicating a change in glue bead direction. In one particular glue bead pattern according to the present invention the distance "a" is about 2.90 inches; the distance "b" is about 1.65 inches; and "c" is 0.13 inches.

Figure 18C:
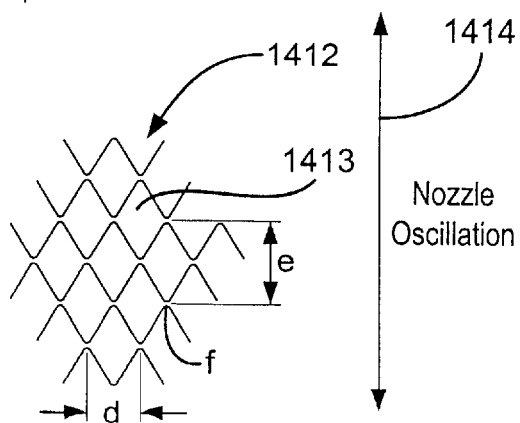

FIG. 18C shows a glue bead pattern 1412 applied by an apparatus as in FIG. 18A (or by one of the apparatuses previously discussed above). The lines in FIG. 18C indicate the center of linear glue beads (any glue bead disclosed herein may be employed for these beads). The distance "d" is the distance between adjacent horizontal vertices (as viewed in FIG. 18C) of a plurality of parallelograms 1413 and the distance "e" is the distance between adjacent vertical vertices (as viewed in FIG. 18C) of the parallelograms 1413. Letter "f" indicates a radius of curvature of a curve indicating a change in direction of a glue bead. In one particular glue bead pattern according to the present invention the distance "d" is about 1.90 inches; the distance "e" is about 3.30 inches; and "f" is 0.13 inches. It is within the scope of certain embodiments of this invention for the radius of curvature (e.g. dimension "c" or "f") to range between 0.01 inches and 3 inches.

As with the arrow 1408, FIG. 18A, the arrow 1414 in FIG. 18C indicates the direction of movement of the movable nozzle manifolds to produce the pattern 1412 (and the pattern 1410, FIG. 18B). With appropriate settings for the speed of movement of screening material beneath the manifolds of the apparatus 1400 and appropriate speed of movement of the movable manifolds a desired glue bead pattern may be produced.

FIG. 19A shows screening material 1420 to which has been applied a glue bead pattern 1425 using an apparatus according to the present invention, including, but not limited to an apparatus like the apparatus 1400, FIG. 18A or any other apparatus disclosed herein. It is to be understood that any desirable glue bead pattern could, according to the present invention, be applied to the screening material 1420. Lines 1421, 1422, 1423, and 1424 indicate the center line of linear a glue beads applied, e.g., by a manifold like the manifold 1403, FIG. 18A, with four glue nozzles (or a manifold with more than four nozzles, but with only four of them operative for this method). Alternatively, according to the present invention, the glue beads whose centers are the lines 1421–1424 may be applied before or after the screening material 1420 is fed beneath the movable nozzles that produce the pattern 1425 (which is to be understood as extending across substantially all of the screening material 1420 although shown only partially on three sections thereof in FIG. 19A).

The lines 1421–1424 are shear lines along which the screening material 1420 may be cut following glue pattern deposition thereby producing three sheets of glue-patterned screening material each of desired width "g". Thus three sheets are produced (of any desired length) which each has a glue bead along its spaced apart sides following shearing of the screening material along the lines 1421–1424. In one particular aspect the distance "g" is about 11.75 inches and the distance "h" is about 1.38 inches.

FIG. 19B shows screening material 1426, like the screening material 1420, with entire glue beads 1427–1429, 1439 illustrated, each with a shear line down the glue bead. FIG. 19C shows the screening material 1426 also with vertical (as viewed in FIG. 19C) spaced-apart glue beads 1430, 1431 with shear lines 1432, 1433. With such beads 1430, 1431 screening material sections are produced with ends having a glue bead edge, e.g. as the ends 1434, 1435 of the section 1436. The screening material 1426 has a glue bead pattern 1438 which may be any suitable glue bead pattern and may be any glue pattern disclosed herein. The glue beads 1430, 1431 may be applied with any suitable apparatus as described above. Alternatively they may be applied manually. Any glue bead disclosed herein may be applied manually to a substrate or to screening material.

Figure 19D:
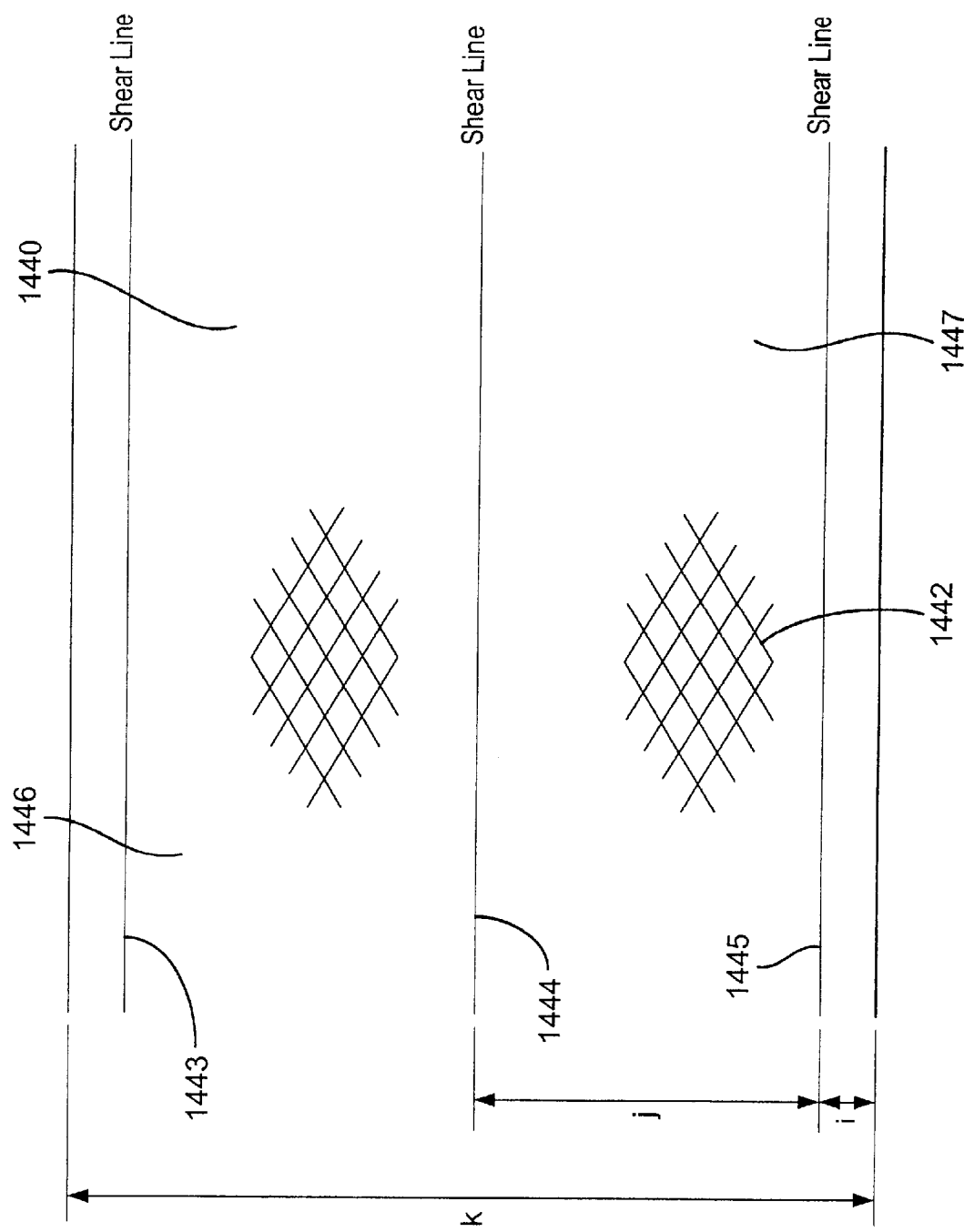

Although FIGS. 19A–19C illustrate a method in which three screen sub-sections extend across the width of the initial sheet of screening material, it is within the scope of this invention to produce one, two, four, five, or more screens from one initial width of screening material. FIG. 19D illustrates screening material 1440 which has a glue pattern 1442 applied thereto according to the present invention. Three glue beads (not shown in their entirety) each have a shear line 1443, 1444, 1445. Upon shearing of the screening material 1440 along the shear lines 1443–1445, two screen sections 1446, 1447 will be produced. In one particular aspect the distance "i" is about 2.50 inches; the distance "j" about 16.50 inches; and the distance "k" about 38 inches. Any pattern may be used for the glue pattern 1442. It is within the scope of this invention to apply glue beads to form glued screen section ends as with the glue beads 1430, 1431 in FIG. 19C.

Screening material and/or a substrate on which glue is to be deposited (either manually with a glue gun or other dispenser, or by automated glue application apparatuses as described herein) may be moved beneath such apparatus or dispenser at a movement rate between 6 inches per minute and 50 feet per minute. In certain other embodiments this rate is between 5 feet per minute and 30 feet per minute.

In other embodiments of the present invention a glue pattern is applied to a substrate other than a screen or mesh or combination or multiple thereof. In certain embodiments the glue pattern on the substrate remains on the substrate and the glue/substrate combination is used with or on one or with, on, or between more than one layer of screen or mesh to form a screen assembly. In other embodiments the glue pattern, e.g. in a cured, semi-cured, or incompletely cured state, is separated from the substrate and applied between, to or on a layer or layers of screen and/or mesh to form a screen assembly. It is within the scope of this invention for such embodiments to employ any suitable glue, including but not limited to thermoplastic and/or thermosetting glues. Any suitable substrate may be employed, including but not limited to, paper, cardboard, kraft paper, wax paper, waxed cardboard, release liner material, and material from which glue is separable without deforming or destroying the glue and without adversely affecting a desired glue pattern; and such material may be used within a roll of screening material glued according to the present invention to prevent the screening material from adhering to itself within the roll, particularly within a roll of screening material in which glue, e.g., hot melt moisture-curing glue is continuing to cure.

In certain embodiments a sheet or piece of a glue/substrate combination or a glue pattern separated from a substrate is formed into a roll of material (with glue to the outside or glue to the inside when the substrate is included) which is then used in the formation of a screen assembly. A glue/substrate combination or separated glue pattern according to the present invention may, according to the present invention, be used to make a screen assembly in any known manner in which pressure and/or heat is applied to a combination of one or more of them with one or more layers of screen and/or mesh.

FIG. 20 shows a glue/substrate combination 1450 with a paper substrate 1452 and a glue pattern 1454 deposited thereon (e.g. by any apparatus and by any method disclosed herein, by hand, or by any suitable machine or apparatus; using any glue suitable for sue in a screen assembly for a vibratory separator). Alternatively the pattern may be any desired pattern including any pattern disclosed herein, with or without edges and/or with or without one or more shear lines of glue.

FIG. 21A illustrates a roll 1451 of the glue/substrate combination 1450 of FIG. 20. As shown the roll is rolled with the substrate on the roll's exterior and the glue pattern disposed internally of the roll; but it is within the scope of this invention for the position of these components to be reversed (as is true of any roll of material according to the present invention), e.g. as shown in FIG. 21B. Such a roll (and any roll of material described herein) may be unrolled for subsequent use. In certain aspects, as needed, such a roll of material may be heated to facilitate its unrolling.

FIG. 22A illustrates a piece of release liner material 1462 (or wax paper or waxed cardboard) to which a glue pattern is to be applied. FIG. 22B shows a resulting glue pattern 1464 applied to the release liner material 1462. FIG. 22C shows the resulting layer of glue pattern 1464 after it has been separated from the substrate of release liner material 1462. The layer of glue pattern 1462 may be used flat as shown in FIG. 22C; or as shown in FIG. 22D it can be rolled into a roll 1461 for further future use.

FIG. 23A shows a screen assembly 1470 according to the present invention with a glue pattern 1474 according to the present invention that has been separated from a substrate to which it was previously applied. The glue pattern 1474 has been applied onto a layer (or layers) of screening material 1473. According to the present invention the glue pattern 1474 (any glue pattern according to the present invention) may be pressed onto and/or into the screening material 1473 and/or heat may be applied to the combination of glue pattern and screen layer to fuse and/or connect the two together and/or to impregnate the screening material 1473 with some or all of the glue pattern 1474. The screening material 1473 may be any screen, screens, mesh, or meshes, or any combination thereof. The glue pattern and screen layer(s) may be pressed together in any suitable manner; e.g., but not limited to, between dual opposed pressing rollers, by a flat plate (heated or not) placed on top of the combination; and/or between the flat plates of a press apparatus.

FIG. 23B shows a screen assembly 1480 according to the present invention which has a glue pattern layer 1484 (like the glue pattern 1474, FIG. 23A or any of its alternative versions) between two screen layers 1483, 1485 (each like the screen layer 1473, FIG. 23A or any of its alternative versions). FIG. 23C illustrates a screen assembly 1490 with two glue pattern layers 1494, 1496 (each like the glue pattern layer 1474, FIG. 23A, or any of its alternative embodiments). A screen layer 1493 (like the screen layer 1473, FIG. 23A or any of its alternative embodiments) is disposed between the glue pattern layers 1494, 1496. The components of the screen assemblies of FIGS. 23B and 23C may be heat treated and/or pressure treated as are the components of the screen assembly 1470, FIG. 23A, as described above.

FIG. 23D shows a screen assembly according to the present invention with a screening material layer 1499 on either side of which are glue pattern layers 1495 and 1497. Each glue pattern layer has not been separated from a substrate 1492, 1498 respectively on which the glue pattern layers have been previously deposited. The screening material layer 1499 may be any screening material disclosed herein. The substrates 1492, 1498 may be any substrates disclosed herein. In one particular embodiment the substrates are suitable cardboard release material (e.g. waxed) which serves as a protective cover or package (with ends appropriately folded over and/or sealed) for the resulting screen assembly. Such cardboard may be sized and of such a nature to withstand any heat treatment and/or pressure treatment to the glue/screening material combination.

It is within the scope of this invention for any screen assembly described herein that includes a glue pattern layer to include a substrate on which the glue pattern layer is formed. The substrate is subsequently removed from the resulting screen assembly by peeling it away, by burning, by chemical degradation (chemical applied with or without pressure) or by liquid (e.g. water) blasting. In any embodiment of a screen assembly herein that employs a glue/substrate combination in the screen assembly, the substrate side or the glue pattern side may be on the exterior on either top or bottom (or both) of the screen assembly. It is also within the scope of this invention for the substrate to include multiple layers of similar or different material. Also, any glued screen layer or layers may be rolled up into a roll according to the present invention with a separator sheet or release liner material under the layer or layers so that screen does not touch screen in a resulting roll of screening material. When curing glue is in such a roll, using such a separator or liner prevents undesired gluing together of screening material within the roll.

"Screening material" for any screen or screen assembly disclosed herein may be any screening material(s) and/or layer(s) disclosed or referred to herein and it may, optionally, be corrugated following glue application. Such corrugation may be in the form of any corrugated screen disclosed in the prior art for use on vibratory separators or shale shakers.

The present invention, therefore, provides in certain, but not necessarily all embodiments, a method for making a screen for a vibratory separator (e.g. but not limited to a screen assembly for a shale shaker for treating drilling fluids), the method including placing at least one layer of screening material below a glue application apparatus, the glue application apparatus including a main body and a plurality of movable glue nozzles movably connected to the body, and applying with the movable glue nozzles an amount of glue flowing from the glue nozzles in a pattern to at least a portion of the at least one layer of screening material by moving the movable glue nozzles over the at least one layer of screening material. Such a method may include one or some of the following, in any possible combination: wherein the glue application apparatus includes at least one glue nozzle secured immovably to the main body, the method including applying with the at least one glue nozzle secured immovably to the main body at least one shearable glue bead having a length to the screening material so that shearing the screening material along the length of the at least one shearable glue bead produces separate sections of the screening material; shearing the screening material along the length of the at least one shearable glue bead; wherein the at least one glue nozzle secured immovably to the main body is a plurality of spaced-apart glue nozzles, each for applying a separate shearable glue bead to the screening material, the method including applying a plurality of spaced-apart shearable glue beads to the screening material; shearing the screening material along the length of each of the plurality of spaced-apart shearable glue beads producing a plurality of separate sections of screening material; wherein the at least one shearable glue bead is sheared into two bead portions, each bead portion at an edge of a resulting separate section of the screening material; wherein each of the plurality of spaced-apart shearable glue beads is sheared into two bead portions, each bead portion at an edge of a resulting separate section of the screening material; wherein the at least one shearable glue bead is a plurality of at least four spaced-apart shearable glue beads in two spaced-apart pairs of glue beads so that shearing along the length of the at least four spaced-apart glue beads produces at least one four-sided screen with a portion of each glue bead along an edge of each of the four sides of the at least one four sided screen, the method including shearing along the length of all four glue beads to produce the at least one four sided screen; wherein the plurality of at least four spaced-apart shearable glue beads is a plurality of spaced-apart shearable glue beads of sufficient number to produce from the screening material a plurality of four-sided screens by shearing each of the plurality of spaced-apart shearable glue beads, the method including shearing along the length of all spaced-apart shearable glue beads to produce the plurality of four-sided screens; continuously moving the at least one layer of screening material beneath the glue application apparatus; wherein the rate of movement of the at least one layer of screening material beneath the glue application apparatus is between 5 feet per minute to 30 feet per minute; and/or connecting the resulting screen or screen assembly to one or more frame members or strip support(s) with or without one or more hookstrip edges or other mounting structure.

The present invention, therefore, provides in certain, but not necessarily all embodiments, a method for making a glue pattern for a shale shaker or other vibratory separator, the method including placing a substrate material below a glue application apparatus, the glue application apparatus including a main body and a plurality of movable glue nozzles movably connected to the body, and applying with the movable glue nozzles an amount of glue in a pattern to at least a portion of the substrate material by moving the movable glue nozzles over the substrate material. Such a method may include one or some of the following, in any possible combination: wherein the glue application apparatus includes at least one glue nozzle secured immovably to the main body (with or without the movable glue nozzles of the preceding sentence), the method including applying with the at least one glue nozzle immovably secured to the main body at least one shearable glue bead to the substrate material so that shearing along a length of the at least one shearable glue bead produces separate sections of the screening material; applying the at least one shearable glue bead to the substrate material, and shearing the substrate material along a length of the at least one shearable glue bead; wherein the at least one shearable glue bead is sheared into two bead portions, each bead portion at an edge of a resulting separate section of the screening material; and/or continuously moving the substrate material beneath the glue application apparatus (e.g. at a rate of between 6 inches a minute to 50 feet a minute or between five and thirty feet a minute).

The present invention, therefore, provides in certain, but not necessarily all embodiments, a method for making a screen for a vibratory separator, the method including placing at least one layer of substrate material below a glue application apparatus, the glue application apparatus including a main body and a plurality of movable glue nozzles movably connected to the body, applying with the movable glue nozzles an amount of glue in a pattern to at least a portion of the layer of substrate material by moving the movable glue nozzles over the at least one layer of screening material, wherein the glue application apparatus includes at least one glue nozzle secured immovably to the main body, applying at least one shearable glue bead having a length to the substrate material, wherein the at least one glue nozzle is a plurality of spaced-apart stationary glue nozzles, each for applying a shearable glue bead to the substrate material, the method further including applying a plurality of spaced-apart shearable glue beads to the substrate material, resulting in a glue pattern member, separating the resulting glue pattern member from the substrate and applying it to screening material, shearing the screening material along the length of each of the plurality of spaced-apart shearable glue beads producing a plurality of separate sections of screening material, wherein each of the plurality of spaced-apart shearable glue beads is sheared into two bead portions, each bead portion at an edge of a resulting separate section of the screening material.

Figure 24A:
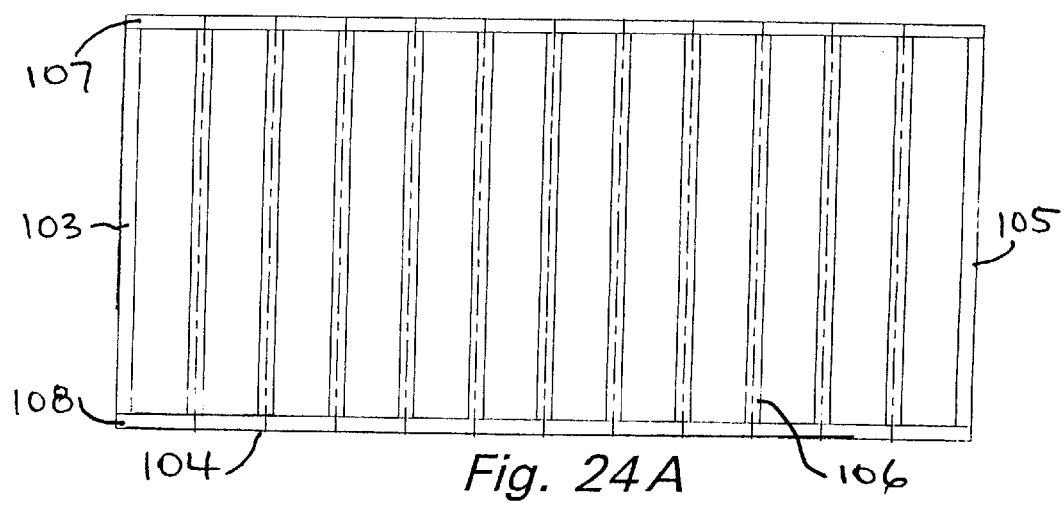
FIG. 24A is a top view of a frame of the screen assembly of FIG. 24C
Figure 24B:
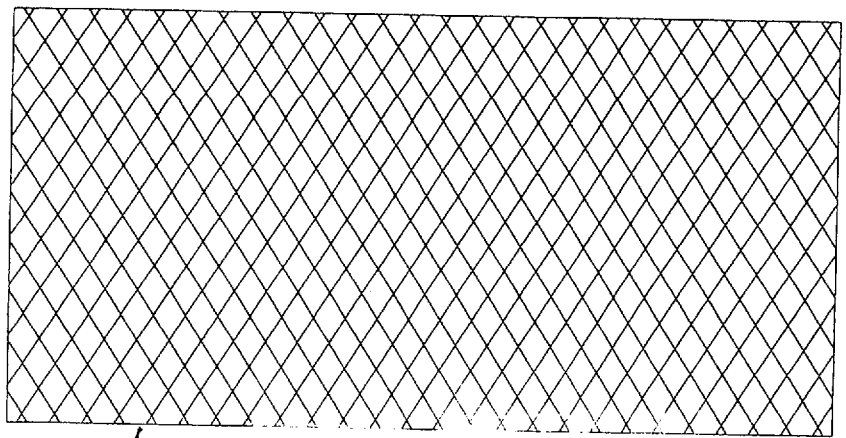
FIG. 24B is a top view of screening material of the screen assembly of FIG. 24C.
Figure 24C:
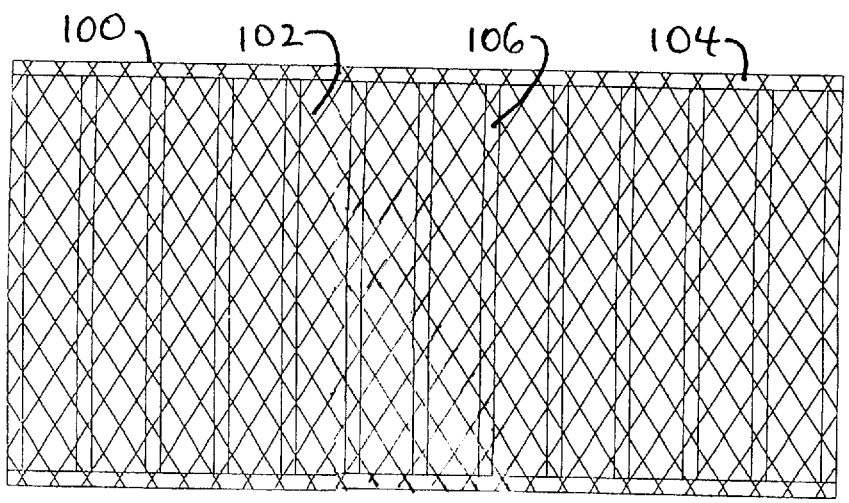
FIG. 24C is a top view of a screen assembly for a vibratory separator according to the present invention.

FIG. 24C shows a screen assembly 100 according to the present invention which has screening material 102 (FIG. 24B) secured onto a tubular frame 104 (FIG. 24A). In other aspects, the frame 104 is deleted. In other aspects the frame 104 is deleted and a hookstrip is connected to each of two spaced-apart sides of the screening material 102. The screening material is any multi-layer screen according to the present invention with two, three or more layers glued together as described herein according to the present invention. The screening material 102 and the tubular frame 104 are encapsulated with a powdered epoxy in a semi-cured state. The frame 104 and the screen material 102 are placed on a heated platen. The currently semi-cured powdered epoxy is heated to a flowable state (e.g. to 300 degrees F.–500 degrees F.). The screen material 102 area adjacent to the frame is thus encapsulated in the powdered epoxy. After about 5 to 10 minutes of heat and pressure (e.g. about 2250 to 400 p.s.i.) the screen material 102 and frame 104 are removed and allowed to cool down to ambient room temperature. The cured powdered epoxy encapsulates the screen material, adjacent to the frame and the frame forming a unitary structure. Coating thickness to achieve good encapsulation, in certain aspects, is between 20 and 40 mils.

The tubular frame 104 has a plurality of crossmembers 106 that extend between and whose ends are connected to sides 107, 108 of the frame 104. End members 103, 105 are at the ends of the frame 104. The tubular frame 104 and its parts may be made of hollow or solid beams, tubes, bars, or rods of metal (e.g. steel, aluminum, zinc, stainless steel and/or alloys of any of these), plastic, or fiberglass. Metal and/or plastic parts may be welded together.

In one particular aspect the frame 104 is made of hollow square cross-section tubes 103, 104, 107, 108 with a 0.766 inch square cross-section and round cross-section tubes 106 with a 0.601 square inch cross-section. The screen assembly 100 (and the frame 104) may have any suitable desired length and width. In one aspect the screening material is made of strands of 304, or 316 stainless steel and the frame is made of carbon steel; thus, the frame does not expand as much as the screening material during a heating step during which epoxy is being applied and the setting epoxy holds the stainless steel strands in an expanded state so the screening material, upon cooling of the screen assembly, is held in tension over the frame 104.

In one aspect the screening material is bonded to the frame with a powdered epoxy material. The frame is heated then dipped into a fluidized bed of the powder which completely encapsulates the frame in a semi-cured state and, in one particular aspect, with a thickness of about 35 mils. The frame and screening material are put on a heated platen with the screening material (in one case three layers 170× 105 mesh, 105×64 mesh and 19 mesh glued together with a method according to the present invention) below the frame. Upon heating to about 450 degrees F., the powdered adhesive is heated and flows down over the wires of the screening material. In one aspect the wires are partially coated and in another they are, preferably, completely encapsulated with the adhesive. The frame with the screening material on it is left on the heated platen until the coating is cured, being heated when it is curing. In one aspect the coating encapsulates the frame.

Figure 25:
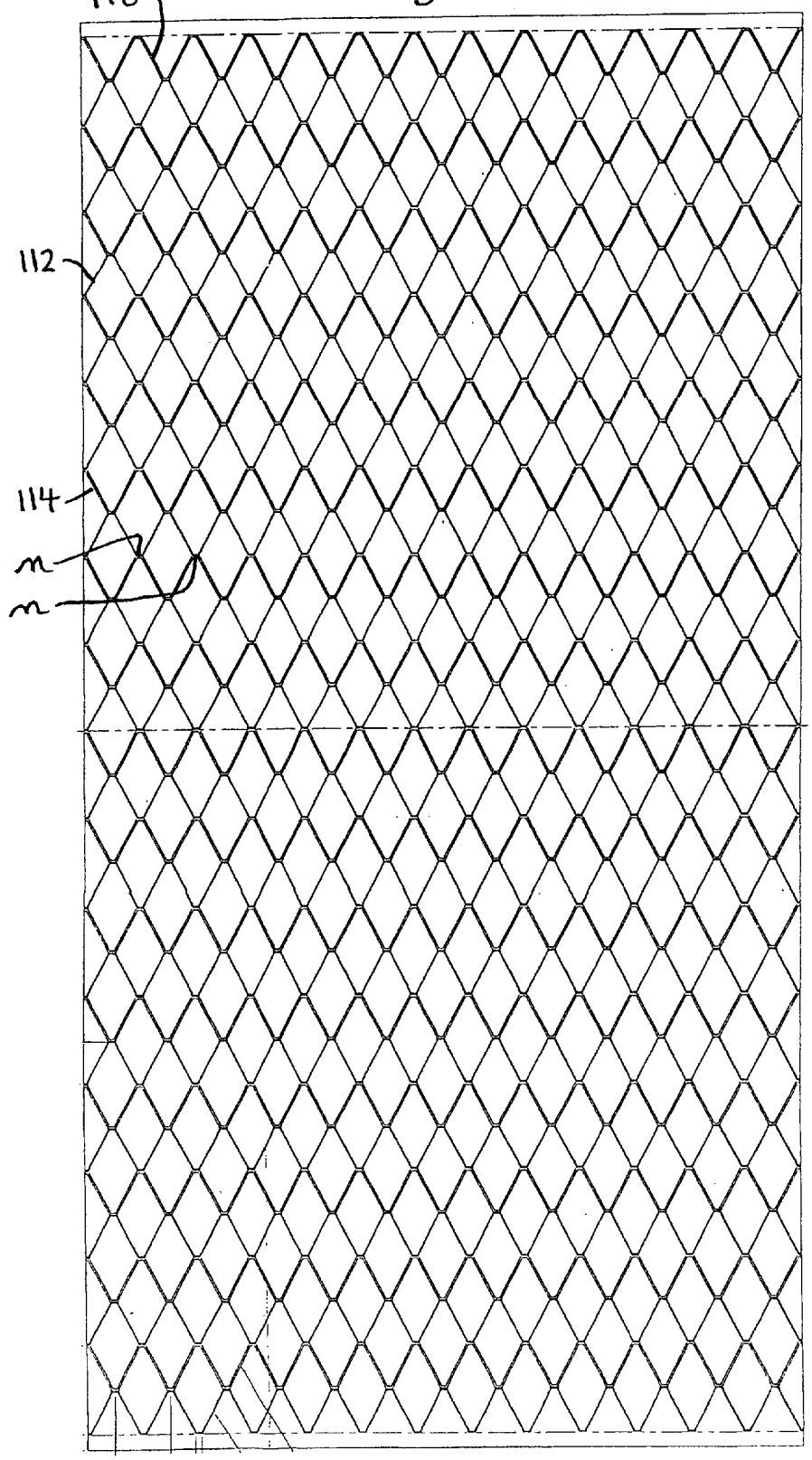
FIG. 25 is a top view of a screen assembly for a vibratory separator according to the present invention.

FIG. 25 shows a glue bead pattern 110 made by a machine according to the present invention with two moving manifolds, each with a plurality (in one aspect, sixteen) of spaced-apart glue dispensing nozzles. The manifolds are moved across the screening material (from left to right in FIG. 25) dispensing beads of moisture-cure hot melt glue. The dark lines 112 represent a glue bead applied by the glue dispensers of a first manifold and the open lines 114 represent a glue bead applied by the glue dispensers of a second manifold. The screening material is moving beneath the moving manifolds and, thus, the pattern shown in FIG. 25 is achieved. Specific machines and methods useful in producing such a pattern are described above and in the application entitled "Methods and Machines For Making Glued Shale Shaker Screens" filed on even date herewith. In one particular embodiment of a glue pattern as shown in FIG. 25, the pattern is applied on coarse mesh, e.g. about 19 mesh, about 50 inches wide, with the total pattern width being about 49 inches. The coarse mesh is unrolled continuously from a roll of about 600 feet in length (although the use of shorter and of longer rolls is within the scope of this invention) and moved continuously past and beneath the glue manifolds. The manifolds in this particular embodiment move about 1.46875 inches back and forth and the distance between two nodes n is about 1.90 inches. The nodes themselves, which can be any desired length, are about 0.20 inches long in this particular embodiment. In certain aspects, the hot melt glue is sufficiently viscous that it remains on top of the mesh or screening layer to which it is applied without falling away from it so a pattern is maintained and multiple layers can be glued together.

FIGS. 26A–28G are top views of glue patterns according to the present invention. In certain aspects such glue patterns are applied by methods and machines described herein and in the application entitled "Methods and Machines For Making Glued Shale Shaker Screens" co-owned herewith, fully incorporated herein for all purposes, appended hereto, and the application for patent with respect to which was filed on the same date as the application for the patent on the present invention. It is to be understood that the patterns shown are repeated across an entire surface of screening material and that the bead width, node length, node width, and intersection dimensions may be any desired dimensions, length, width, and/or height.

Figure 26A:
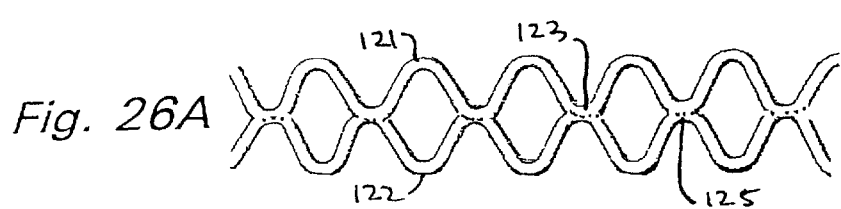
FIGS. 26A–26I are top views of glue patterns according to the present invention.
Figure 26B:
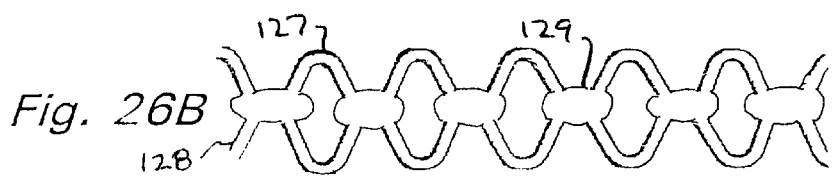

FIG. 26A shows a glue pattern 120 which includes undulating glue bead lines 121, 122 with crests 123 of the glue bead line 121 superimposed on similar crests 125 of the glue bead line 122. Thus at the location of this superimposition there is more glue present than there is at other places in the glue bead lines 121, 122; thus these points of superimposition are stronger than other points along these glue bead lines. As shown in FIG. 26B, there is significantly more glue at locations 129 of intersection of glue bead lines 127, 128 and the locations of intersection have a distinct oval or elliptical shape.

Figure 26C:
Figure 26D:
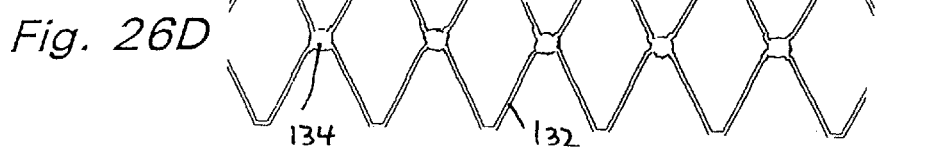

FIG. 26C shows a pattern 120 like that in FIG. 25; but in FIG. 26D the crests or nodes of glue bead lines 131, 132 of a pattern 133 are overlapped or superimposed so that generally circular (as viewed from above) intersection locations 134 are formed.

Figure 26E:
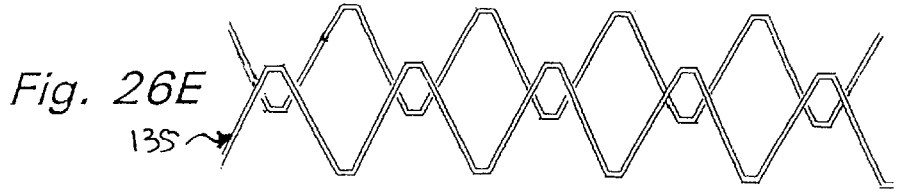
Figure 26F:
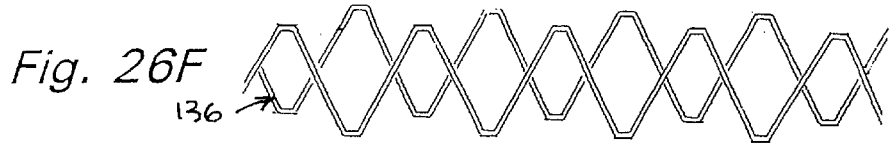
Figure 26G:
Figure 26H:
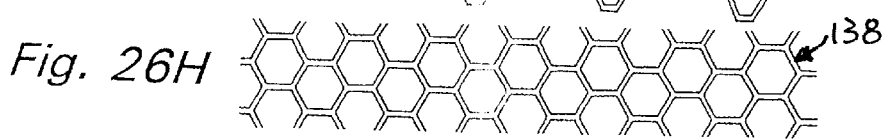
Figure 26I:
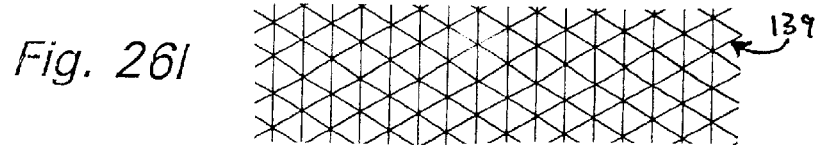
Figure 27A:
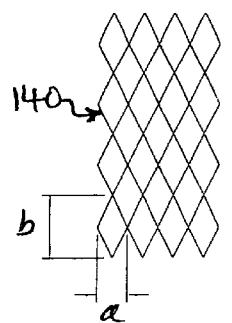
FIGS. 27A–27D are top views of glue patterns according to the present invention.

FIGS. 26E–26G illustrate glue bead patterns 135, 136, 137, 138 and 139 respectively, formed by intersecting glue bead lines from two spaced-apart glue-dispensing manifolds and/or glue dispensing nozzles according to the present invention. Of course it is within the scope of this invention to produce glue bead patterns with three, four or more spaced-apart manifolds of glue dispensers.

Figure 28A:
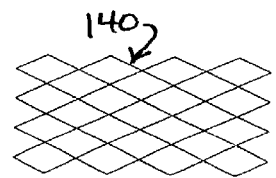
FIGS. 28A–28D are top views of glue patterns according to the present invention.

FIGS. 27A–27D illustrate glue bead patterns according to the present invention applicable to screening material by methods and machines according to the present invention. A pattern 140, FIG. 27A, in one particular embodiment, has a distance "a" between pattern intersection points of about 1.46875 inches and a distance "b" between pattern intersection points of about 2.9 inches. As shown in FIG. 28A, (and as is true for any glue bead pattern disclosed herein) the pattern 140 may be turned ninety degrees for application to screening material. Also any screen assembly made with any pattern disclosed herein may have fluid introduced to any side of any such screen assembly.

Figure 27B:
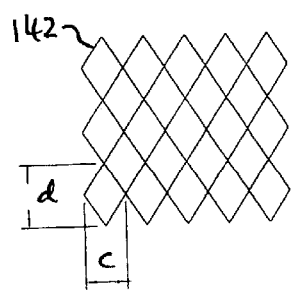
Figure 28B:
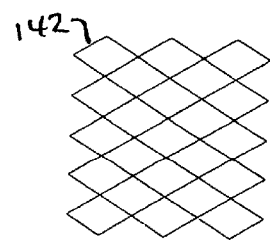

A pattern 142, FIG. 27B, in one particular embodiment, has a distance "c" between pattern intersection points of about 1.9 inches and a distance "d" between pattern intersection points of about three inches. As shown in FIG. 28B, the pattern 142 may be turned ninety degrees for application to screening material.

Figure 27C:
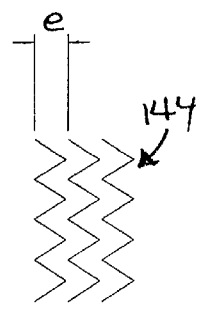
Figure 28C:

As shown in FIG. 27C a pattern 144 according to the present invention has glue bead lines that do not intersect. A distance "e", in one particular embodiment, between lines is about 1 19/32 inches. FIG. 28C shows that the pattern 144 may be turned ninety degrees if desired.

Figure 27D:
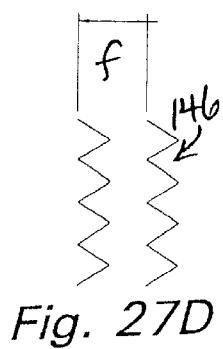
Figure 28D:
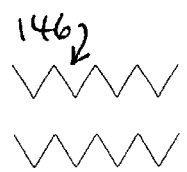
Figure 29A:
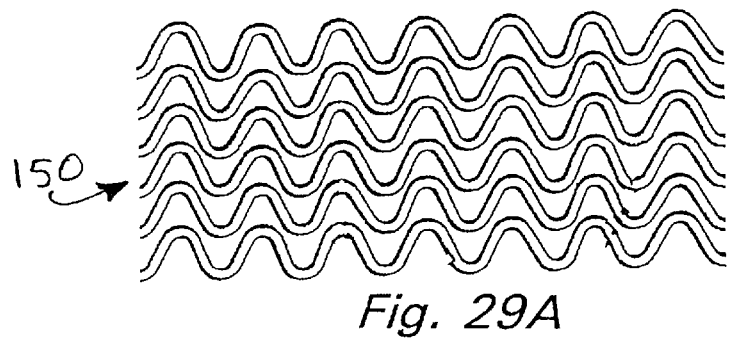
FIGS. 29A–29K are top views of glue patterns according to the present invention.
Figure 29B:
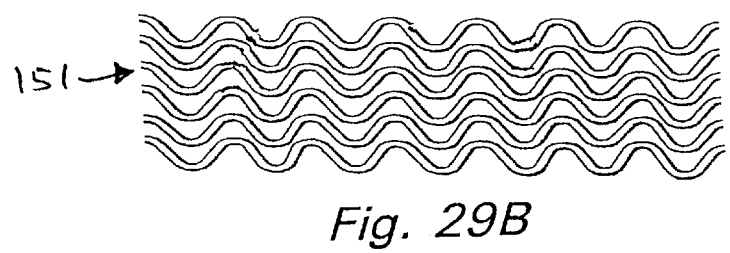
Figure 29C:
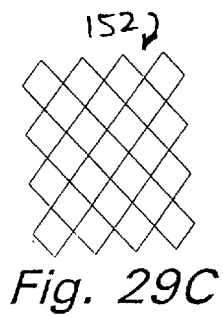
Figure 29D:
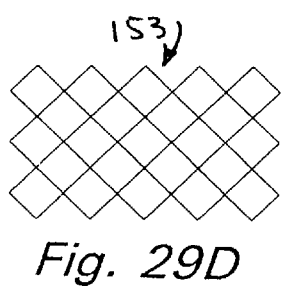
Figure 29E:
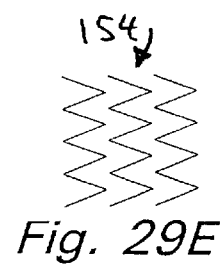
Figure 29F:
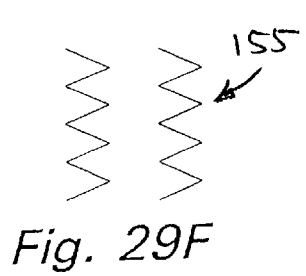
Figure 29G:
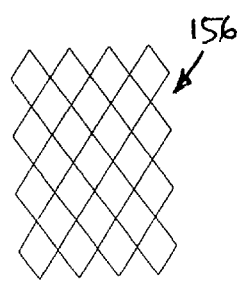
Figure 29H:
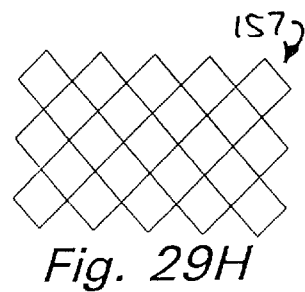
Figure 29I:
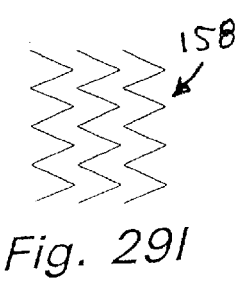
Figure 29J:
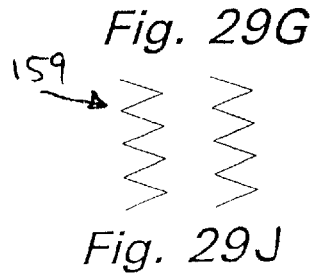
Figure 29K:
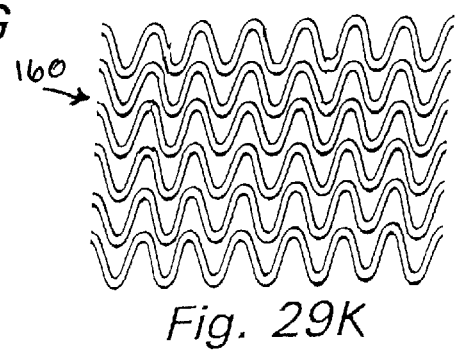

FIG. 27D shows a pattern 146 according to the present invention which has non-intersecting glue bead lines. A distance "f", in one particular embodiment, between lines is about 3 1/16 inches. FIG. 28D shows the pattern 146 turned ninety degrees.

FIGS. 29A–29K are top views of glue bead patterns 150–160, respectively, according to the present invention.

Any glue bead pattern shown herein may, according to the present invention, be produced with bead lines overlapping to form intersections, e.g. like those of FIGS. 26A–26D.

Figure 30A:
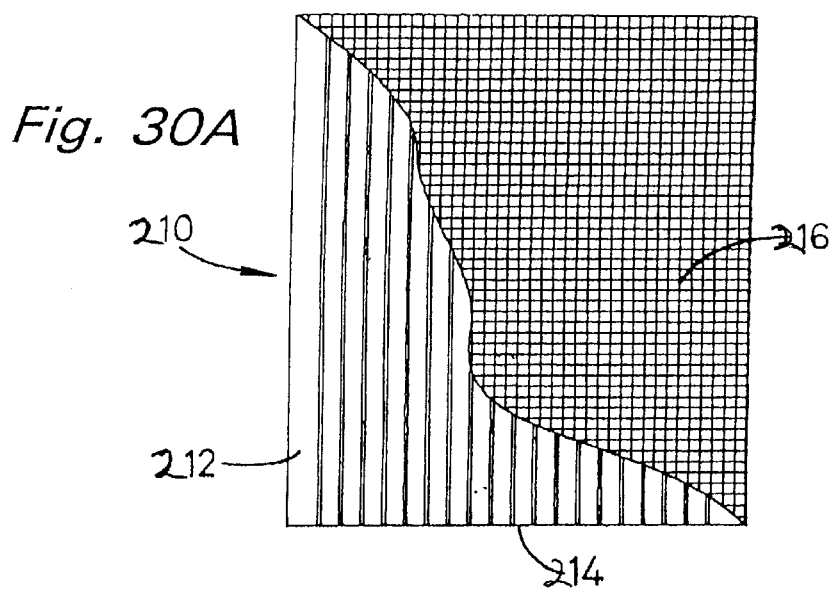
FIG. 30A is a top view partially cut-away of a screen according to the present invention.

FIG. 30A shows a screen 210 according to the present invention with a lower base, support or frame 212, three undulating mesh screens 214 on and/or bonded to the frame 212, and an upper mesh or screen 216. The screens 214 may themselves be mechanically connected together and/or bonded together, e.g. with epoxy, welding, and/or sintering. Rubber strips, plastic strips tape, cushion or cushions 218 are positioned between the screen 214 and the upper screen 216. The strip(s) or cushion(s) are optional. As shown the strip(s), tape(s), or cushion(s) 218 are secured to the screen 214 (or to crests thereof), but it is within the scope of this invention to secure them (or some of them) to the screen 216. To effect such securement any suitable glue, epoxy, weld, and/or sintering may be employed. The frame 212 may be any suitable known base, frame or support.

Figure 30B:
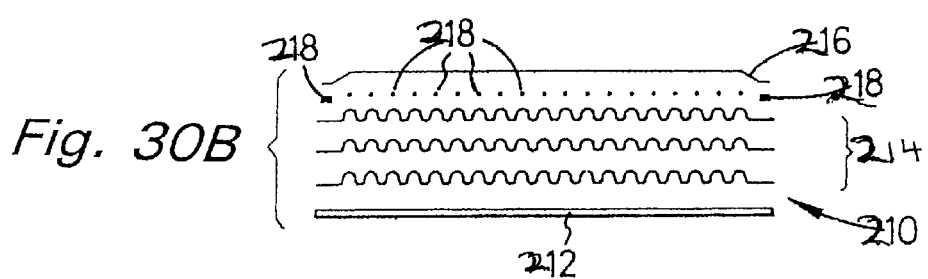
FIG. 30B is an exploded view of the screen of FIG. 30A.

It is within the scope of this invention for the screen 214 to be any known screen, mesh, screens, meshes, or combination thereof, mechanically connected together and/or bonded together, unbonded, or bonded at only certain locations and with any known shape as viewed either from above or on end (as in FIG. 30). It is within the scope of this invention for the upper screen 216 to be any known screen, mesh, screens, meshes, or combination thereof, connected and/or bonded together or unbonded, and with any known shape. As shown in FIG. 30B, the screen 214 is three mesh screens bonded together with coarser mesh on the bottom, medium mesh in the middle, and finer mesh on top. The screen 216 as shown may be a scalping screen of a mesh coarser than the finest mesh of the screen 214 or of a multi-layer coarser mesh. In another aspect the screen 214 is a single screen of closely woven mesh made of any suitable material, e.g. stainless steel and/or plastic material and the screen 216 is a single screen of coarser mesh made of any suitable material (e.g. but not limited to stainless steel and/or plastic), with the screen 214 on a metal or plastic frame or support. Alternatively or additionally, instead of the frame 212 any known perforated plate, strip, or series of straps or strips may be used. A series of strips is not legally equivalent to a perforated plate.

In one aspect the strips 18 are fused plastic strips aligned with peaks of the undulating fine mesh. Such strips may be made of rubber (e.g. nitrile) or plastic, e.g. polypropylene, to inhibit or prevent abrasion of the finer meshes. Such strips can be glued to the bottom of the screen 216 and/or the screen 214. Also the screen 216 can be glued to the screen 214.

Figure 31:
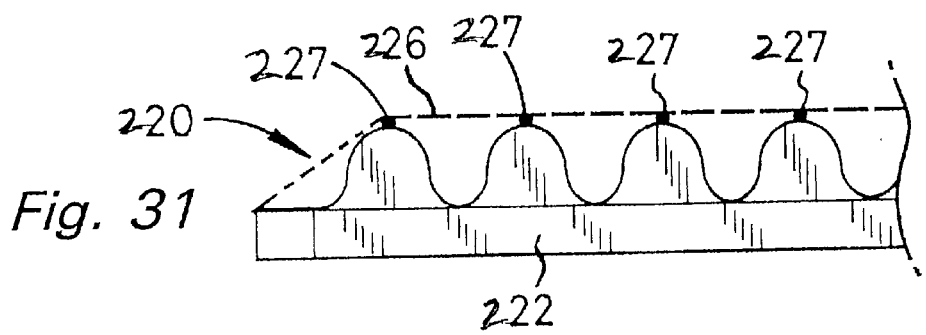
FIG. 31 is an end view of a screen according to the present invention.

FIG. 31 shows a screen 220 like the screen 210, but without the cushion members 218. A scalping screen 226 is secured at points 227 to a screen 224 on a base, frame, or support 222. The screens 224, 226 may be in any of the forms discussed above for the screens 214, 216, respectively and the base, frame, or support 222 may have any of the forms or alternatives discussed above for the base, frame, or support 212. The screen 226 may be secured to the screen 224 in any suitable way, including but not limited to with glue, epoxy, fused plastic and/or by welding and/or sintering.

The present invention, therefore, provides in certain aspects a vibratory shaker system with a basket for mounting at least one screen for screening fluid introduced thereon, vibrator apparatus connected to the basket for vibrating the basket and the at least one screen, the at least one screen like any screen disclosed herein.

Figure 32:
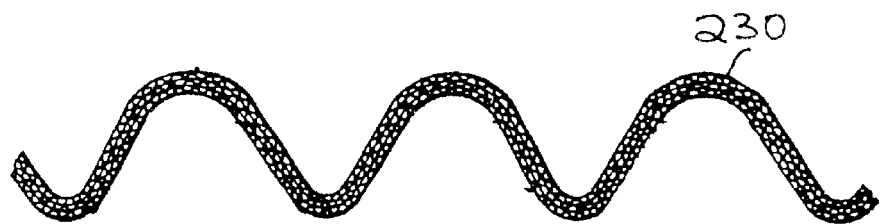
FIG. 32 is a side cross-section view of screening material according to the present invention.

FIG. 32 shows screening material according to the present invention glued together by any apparatus and/or method according to the present invention. The screening material 230 has been corrugated. It is within the scope of this invention to corrugate screening material made according to the present invention for use in any known so-called "three dimensional" screen or screen assembly. One, two, three, four or more combined layers of screening material may be corrugated using any known method and/or apparatus. Such corrugating may be done before or after the curing of glue used to glue layers together.

Figure 33:
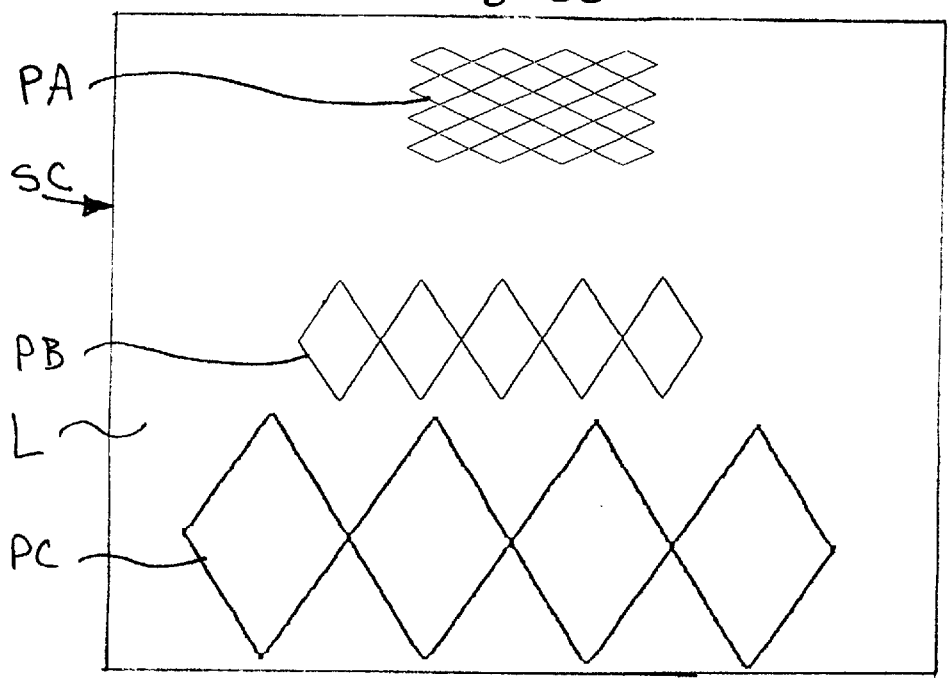
FIG. 33 is a top schematic view of a screen assembly according to the present invention.

FIG. 33 shows a screen assembly SC according to the present invention which has at least one layer of screen material L and a glue pattern that includes sub-patterns PA, PB and PC. Although only portions of the sub-patterns are shown, it is to be understood that they extend from one side of the screen assembly SC to the other and that different sub-patterns have abutting edges so that substantially all of the area (as viewed in FIG. 33 of the screen assembly SC, except for outer boundaries) is covered by the sub-patterns.

As shown in FIG. 33 fluid introduced to the screen assembly SC flows first to the sub-pattern PA area, then on to the sub-pattern PB area, then to the sub-pattern PC area, and the separated material flows off the screen assembly SL (to the bottom of the drawing sheet as shown in FIG. 33). The sub-pattern PA has diamonds that are smaller than diamonds of the sub-pattern PB; and the diamonds of the sub-pattern PB are smaller than diamonds of the sub-pattern PC. Solids on top of the screen assembly SC will tend to move more slowly across the sub-pattern PA area than over the sub-pattern PB area; and solids on top of the screen assembly SC will tend to move more slowly over the sub-pattern PB area than over the sub-pattern PC area. Alternatively (as is true with any screen assembly according to the present invention with any screen assembly according to the present invention with two, three or more sub-pattern areas according to the present invention with a length of screening material between portions of a glue pattern) fluid can be introduced first onto the sub-pattern PC area to flow over the sub-pattern PB area, then to the sub-pattern PA area, and then material on top of the screen assembly SL exits at the edge (top edge as viewed in FIG. 33) of the sub-pattern PA area.

Although diamonds are shown in FIG. 33, any glue pattern disclosed herein may be used with larger or smaller distances between glue portions—larger distances for speeding up solids moving across the screen assembly and smaller distances for slowing the solids movement. Although three sub-pattern areas are shown, two, four or more may be used on any screen assembly according to the present invention. Also, any part of a screen's area may have any sub-pattern; sub-patterns need not extend from one side of a screen assembly to the other.

Figure 34A:
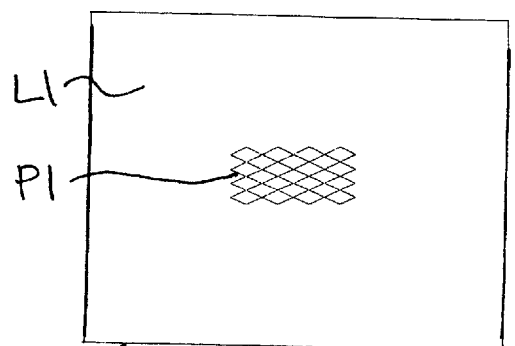
FIGS. 34A–34C are top schematic views of screen assemblies according to the present invention.
Figure 34B:
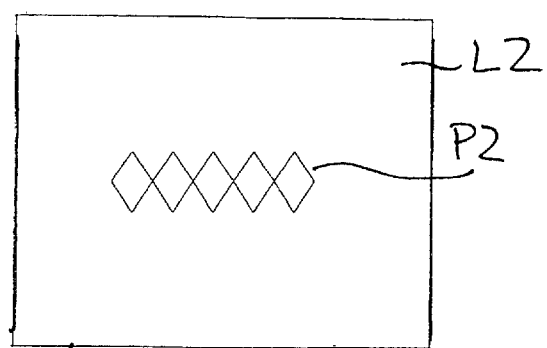
Figure 34C:
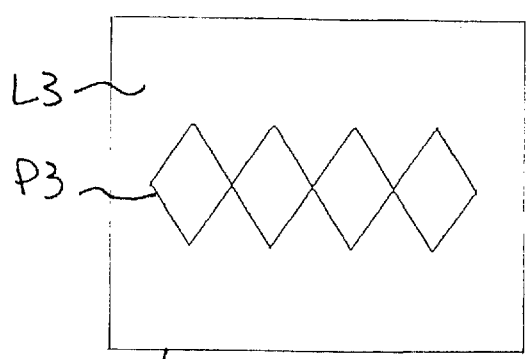

FIGS. 34A–34C illustrate a set of three screen assemblies S1, S2, and S3 according to the present invention, each with at least one layer L1, L2, L3, respectively, of screening material and each with a similar glue pattern, yet with a difference in distance between glue portions of the glue patterns. Such a set (or any two) of the screens S1–S3 may be used on a single vibratory separator or shale shaker when different fluid/solids residence time on top of a screen are desired. Material and/or solids will tend to move slowest across the screen assembly S1 with its glue pattern P1 and fastest across the screen assembly S3 with its glue pattern P3. Material and/or solids will move slower across screen assembly S2 with its glue pattern P2 than across the screen assembly S3.

FIGS. 35A–35D show a screen assembly 240 according to the present invention which has a layer or layers 241 of screening material glued together according to the present invention with hot melt moisture-curing glue. Side hookstrips 242 provide for mounting of the screen assembly 240 in an appropriate vibratory separator or shale shaker.

FIG. 36A shows a support 250 according to the present invention for supporting one or more layers of screening material, including, but not limited to a layer with a glue pattern (any herein) described herein or two, three, four or more layers of screening material glued together as disclosed herein.

The support 250 has two pairs 251, 252 of opposed spaced-apart sides and a plurality of cross-members 253 extending between and attached to the sides 251. Notches may be cut in parts of the sides 251 to receive and hold ends of the cross-members 253.

The sides 251, 252 may be made by cutting from a solid sheet or plate a sub-rectangle out of the complete rectangle (with outer boundaries like those of the support 251, FIG. 36A). Corner cuts are then made and portions 254 at each end and 251a at each side are bent or folded down. One or more dimples 255 projecting downwardly from a side or end raise that end with respect to a rail or other mounting structure of a shaker or separator to facilitate correct emplacement of an adjoining screen's end under the end of a screen assembly with the support 250.

Figure 37A:
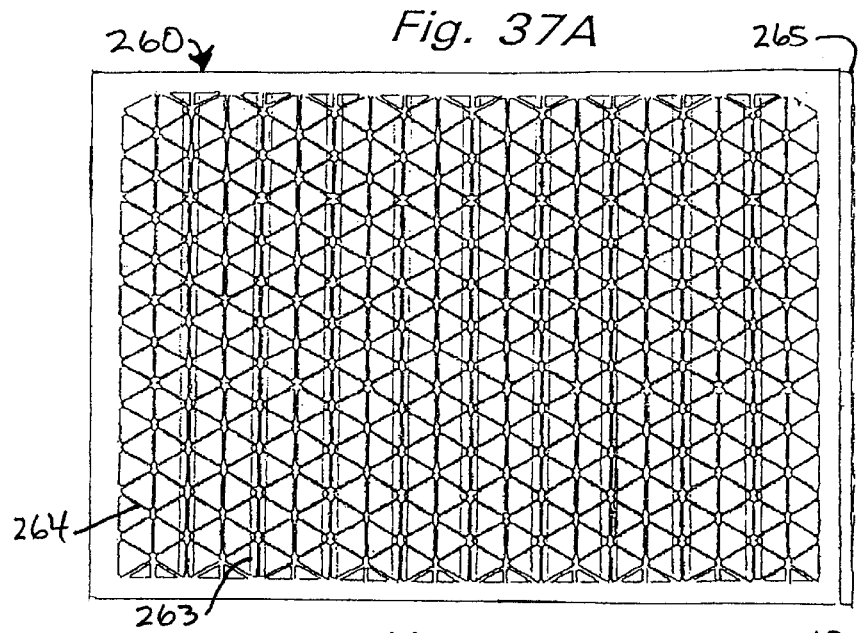
FIG. 37A is a top view of a screen support according to the present invention.
Figure 37B:
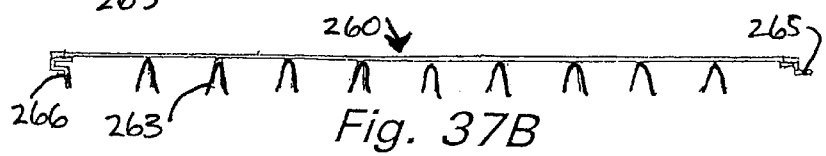
FIG. 37B is a cross-section view along the length of the screen assembly of FIG. 37A.
Figure 37C:
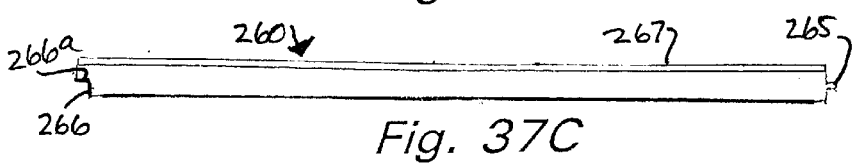
FIG. 37C is a side view of the screen assembly of FIG. 37A.

FIG. 37A shows a support 260 according to the present invention for supporting a layer of screening material with a glue pattern as any disclosed herein. The support 260 is made from a sheet or plate and has a pattern 264 of openings across its surface. A plurality of cross-members extend from one side of the support 260 to the other. A piece 265 at one end of the support 260 has an outer end that projects outwardly from the support 260 and a piece 266 has a shoulder part 266a against which an outer end (like the end of the piece 265) of another screen can be positioned. Layer 267 indicates any screening material or multiple layers thereof according to the present invention or as referred to herein.

Figure 38:
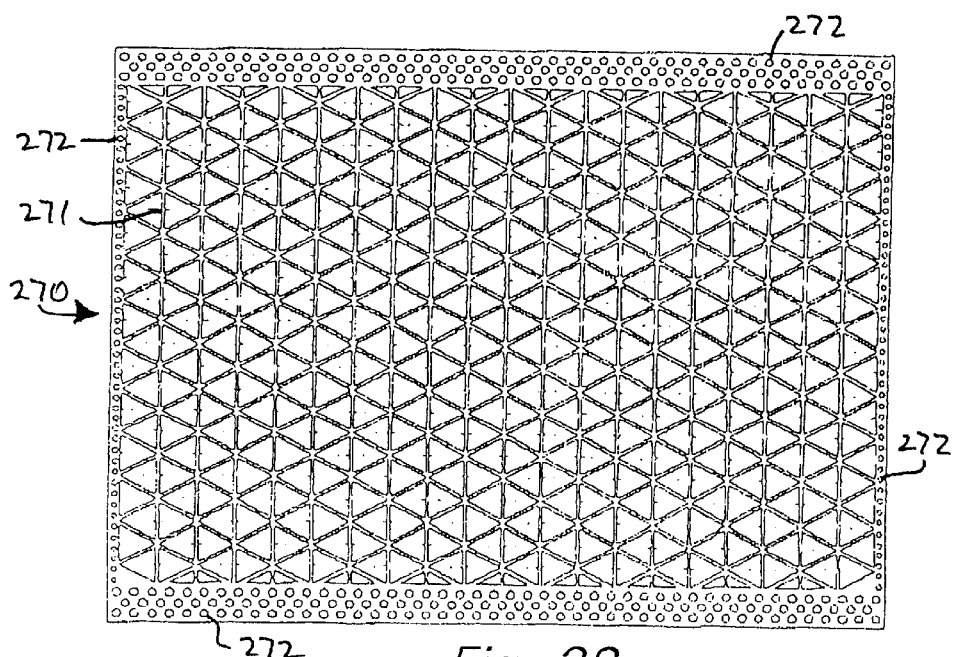
FIG. 38 is a top view of a screen support according to the present invention.

FIG. 38 shows a perforated plate 270 according to the present invention with a pattern of openings 271 across its surface and with a plurality of optional edge holes 272 which facilitate bonding of the plate to other structures and/or bonding of screening material to the plate.

In conclusion, therefore, it is seen that the present invention and the embodiments disclosed herein and those covered by the appended claims are well adapted to carry out the objectives and obtain the ends set forth. Certain changes can be made in the subject matter described, shown and claimed without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form its principles may be utilized.

What is claimed is:

1. A screen assembly made by a method for making a screen assembly for a vibratory separator, the method comprising
    moving with screen movement apparatus at least one layer of screening material below a glue application apparatus, the glue application apparatus including a main body a plurality of movable glue nozzles movably connected to the body,
    moving the movable glue nozzles with nozzle movement apparatus above the at least one layer of screening material,
    applying with the movable glue nozzles an amount of glue flowing from the glue nozzles in a pattern to at least a portion of the at least one layer of screening material, and
    allowing the glue to cure,
    wherein the glue is heated moisture-curing hot melt glue, and
    rolling the at least one layer of screening material in a roll following application of glue thereto.

2. A screen assembly for a shale shaker, the screen assembly made by an automated method, the automated method comprising
    applying glue in a glue pattern to at least one layer of screening material useful for screening fluid introduced to a shale shaker, said applying done by powered moving mechanical glue application means,
    wherein the method includes moving at least one glue dispensing manifold with a plurality of spaced-apart glue dispensing nozzles above the at least one layer of screening material to apply the glue pattern.

3. The screen assembly of claim 2 wherein the glue is heated moisture-curing hot melt glue.

4. The screen assembly of claim 2 wherein moisture is applied to glue in the glue pattern following application of the moisture-curing hot melt glue to the at least one layer of screening material.

5. The screen assembly of claim 2 wherein the automated method further comprising
    moving with powered mechanical screen movement apparatus the at least one layer of screening material beneath the powered moving mechanical glue application means.

6. The screen assembly of claim 2 wherein the at least one layer of screening material is three layers of screening material.

7. The screen assembly of claim 2 wherein the powered moving mechanical glue application means includes a patterned roller having a glue pattern thereon for applying glue in said glue pattern to the at least one layer of screening material.

8. The screen assembly of claim 2 wherein the method includes moving two spaced-apart glue dispensing manifolds each with a plurality of spaced-apart glue dispensing nozzles above the at least one layer of screening material to apply the glue pattern.

9. The screen assembly of claim 2 wherein the screen assembly is mounted on screen assembly support means.

10. The screen assembly of claim 9 wherein the screen assembly support means is from the group consisting of frame, strip support, perforated sheet metal, and perforated plate.

11. The screen assembly of claim 2 further comprising
    hookstrip apparatus on each of two spaced-apart sides of the screen assembly.

12. A screen assembly for a shale shaker, the screen assembly made by an automated method, the automated method comprising
    applying glue in a glue pattern to at least one layer of screening material useful for screening fluid introduced to a shale shaker, said applying done by powered moving mechanical glue application means,
    wherein the screen assembly is mounted on screen assembly support means, and
    wherein the screen assembly support means is from the group consisting of frame, strip support, perforated sheet metal, and perforated plate.

13. A screen assembly for a shale shaker, the screen assembly made by an automated method, the automated method comprising
    applying glue in a glue pattern to at least one layer of screening material useful for screening fluid introduced to a shale shaker, said applying done by powered moving mechanical glue application means, and
    hookstrip apparatus on each of two spaced-apart sides of the screen assembly.

14. A screen assembly made by a method for making a screen assembly for a vibratory separator, the method comprising
    moving with screen movement apparatus at least one layer of screening material below a glue application apparatus, the glue application apparatus including a main body and a plurality of movable glue nozzles movably connected to the main body,
    moving the movable glue nozzles with nozzle movement apparatus above the at least one layer of screening material,
    applying with the movable glue nozzles an amount of glue flowing from the glue nozzles in a pattern to at least a portion of the at least one layer of screening material,
    allowing the glue to cure, and
    combining at least one additional layer of screening material with the at least one layer of screening material, wherein the at least one additional layer of screening material is combined with the at least one layer of screening material following application of glue to the at least one layer of screening material.

15. The screen assembly of claim 14 wherein the glue application apparatus includes at least one glue nozzle secured immovably to a main body, the method further comprising
    applying with the at least one glue nozzle secured immovably to the main body at least one shearable glue bead having a length to the screening material so that shearing the screening material along the length of the at least one shearable glue bead produces separate sections of the screening material.

16. The screen assembly of claim 15 wherein the at least one nozzle secured immovably to the main body is a plurality of spaced-apart glue nozzles, each for applying a separate shearable glue bead to the screening material, the method further comprising
    applying a plurality of spaced-apart shearable glue beads to the screening material.

17. The screen assembly of claim 14 wherein the method further comprises continuously moving the at least one layer of screening material beneath the glue a plication apparatus.

18. The screen assembly of claim 14 wherein a rate of movement of the at least one layer of screening material beneath the glue application apparatus is between 5 feet per minute to 30 feet per minute.

19. The screen assembly of claim 14 wherein the glue is heated moisture-curing hot melt glue.

20. The screen assembly of claim 19 wherein the method further comprises applying moisture to the heated moisture-curing hot melt glue to facilitate curing of it.

21. The screen assembly of claim 14 wherein the method further comprises tensioning the at least one layer of screening material below the glue application apparatus.

22. The screen assembly of claim 14 wherein the method further comprises rolling the at least one layer of screening material in a roll following application of glue thereto.

23. The screen assembly of claim 22 wherein the method further comprises positioning separator material with respect to at least one layer of screening material to prevent undesired gluing together of screening material within the roll.

24. The screen assembly of claim 14 wherein the at least one layer of screening material is a layer of coarse mesh.

25. The screen assembly of claim 14 wherein the pattern includes a plurality of intersections of lines of glue.

26. The screen assembly of claim 14 wherein the method further comprises corrugating the at least one layer of screening material.

27. The screen assembly of claim 26 wherein the method further comprises corrugating the at least one layer of screening material.

28. The screen assembly of claim 14 wherein the glue application apparatus includes at least one glue nozzle secured immovably to a main body, the method further comprising applying with the at least one glue nozzle secured immovably to the main body at least one shearable glue bead across a width of the screening material so that shearing the screening material along the length of the at least one shearable glue bead produces separate sections of the screening material.

29. The screen assembly of claim 28 wherein the at least one nozzle secured immovably to the main body is a plurality of spaced-apart glue nozzles, each for applying a separate shearable glue bead to the screening material, the method further comprising applying a plurality of spaced-apart shearable glue beads to the screening material across the width thereof.

30. A screen assembly made by a method for making a screen assembly for a vibratory separator, the method comprising moving with screen movement apparatus at least one layer of screening material below a glue application apparatus, the glue application apparatus including a main body and a plurality of movable glue nozzles movably connected to the main body, moving the movable glue nozzles with nozzle movement apparatus above the at least one layer of screening material, applying with the movable glue nozzles an amount of glue flowing from the glue nozzles in a pattern to at least a portion of the at least one layer of screening material, allowing the glue to cure, and wherein a rate of movement of the at least one layer of screening material beneath the glue application apparatus is between 5 feet per minute to 30 feet per minute.

* * * * *